US008574831B2

(12) United States Patent
Dehertogh et al.

(10) Patent No.: US 8,574,831 B2
(45) Date of Patent: Nov. 5, 2013

(54) MUTATIONAL PROFILES IN HIV-1 REVERSE TRANSCRIPTASE CORRELATED WITH PHENOTYPIC DRUG RESISTANCE

(75) Inventors: Pascale Alfons Rosa Dehertogh, Puurs (BE); Kurt Hertogs, Antwerpen (BE); Brendan Larder, Cambridge (GB); Dechao Wang, Cambridge (GB)

(73) Assignee: Virco N.V., Mechelen (BE)

( * ) Notice: Subject to any disclaimer, the term of this patent is extended or adjusted under 35 U.S.C. 154(b) by 1029 days.

(21) Appl. No.: 11/933,747

(22) Filed: Nov. 1, 2007

(65) Prior Publication Data

US 2008/0286754 A1    Nov. 20, 2008

Related U.S. Application Data

(63) Continuation of application No. 10/399,920, filed as application No. PCT/EP01/12338 on Oct. 22, 2001, now abandoned.

(60) Provisional application No. 60/241,801, filed on Oct. 20, 2000, provisional application No. 60/241,844, filed on Oct. 20, 2000.

(51) Int. Cl.
C12Q 1/70    (2006.01)
C12Q 1/68    (2006.01)

(52) U.S. Cl.
USPC .............................. 435/6.1; 435/5; 435/6.12

(58) Field of Classification Search
None
See application file for complete search history.

(56) References Cited

U.S. PATENT DOCUMENTS

| | | | |
|---|---|---|---|
| 5,631,128 A | 5/1997 | Kozal et al. | |
| 5,650,268 A | 7/1997 | Kozal et al. | |
| 5,856,086 A | 1/1999 | Kozal et al. | |
| 6,221,578 B1 | 4/2001 | de Bethune et al. | |
| 6,528,251 B2 | 3/2003 | de Bethune et al. | |
| 7,058,616 B1 | 6/2006 | Larder et al. | |
| 7,217,506 B2 | 5/2007 | De Meyer et al. | |
| 7,292,944 B2 | 11/2007 | Larder et al. | |
| 7,473,524 B2 | 1/2009 | Azijn et al. | |
| 7,494,768 B1 | 2/2009 | Hertogs et al. | |
| 2003/0190603 A1 | 10/2003 | Larder et al. | |
| 2004/0033489 A1 | 2/2004 | Larder et al. | |
| 2005/0214744 A1 | 9/2005 | Azjin et al. | |
| 2005/0233312 A1 | 10/2005 | De Meyer et al. | |
| 2005/0239053 A1 | 10/2005 | Azijn et al. | |
| 2009/0061420 A1 | 3/2009 | Azijn et al. | |
| 2009/0162867 A1 | 6/2009 | Hertogs et al. | |

FOREIGN PATENT DOCUMENTS

| | | |
|---|---|---|
| CA | 2029123 A1 | 5/1991 |
| EP | 0406958 A2 | 1/1991 |
| EP | 0422762 A2 | 4/1991 |
| EP | 0428000 A1 | 5/1991 |
| EP | 0518557 A2 | 12/1992 |
| EP | 0824148 A2 | 2/1998 |
| EP | 1605064 A1 | 12/2005 |
| JP | 2002-199890 A | 7/2002 |
| WO | WO-9608580 A1 | 3/1996 |
| WO | WO-9727319 A1 | 7/1997 |
| WO | WO-9727332 A1 | 7/1997 |
| WO | WO-9727480 A1 | 7/1997 |
| WO | WO-9961658 A1 | 12/1999 |
| WO | WO-9961666 A1 | 12/1999 |
| WO | WO-9967417 A2 | 12/1999 |
| WO | WO-9967427 A1 | 12/1999 |
| WO | WO-9967428 A2 | 12/1999 |
| WO | WO-0073511 A1 | 12/2000 |
| WO | WO-0078994 A1 | 12/2000 |
| WO | WO-0078996 A1 | 12/2000 |
| WO | WO-0179540 A2 | 10/2001 |
| WO | WO-0181624 A1 | 11/2001 |
| WO | WO-0195230 A2 | 12/2001 |
| WO | WO-0222076 A2 | 3/2002 |
| WO | WO-0233402 A2 | 4/2002 |
| WO | WO-0238792 A2 | 5/2002 |
| WO | WO-02083657 A2 | 10/2002 |
| WO | WO-2004022523 A2 | 3/2004 |

OTHER PUBLICATIONS

Schmit et al. Resistance-related mutations in the HIV-1 protease gene of patients treated for 1 year with the protease inhibitor ritonavir. AIDS 1996, vol. 10, pp. 995-999.*
Doyon et al. Second locus involved in human immunodeficiency virus type 1 resistance to protease inhibitors. Journal of Virology 1996, vol. 70, No. 6, pp. 3763-3769.*
Smidt et al. A mutation in human immunodeficiency virus type 1 protease at postiion 88, located outside the active site, confers restistance to the hydroxyethylurea inhibitor SC-55389A. Antimicrobial Agents and Chemotherapy 1997, vol. 41, No. 3, pp. 515-522.*
Vacca et al. L-735524: An orally bioavailable human immunodeficiency virus type 1 protease inhibitor. Proceedings from the National Academy of Sciences of USA. 1994, vol. 91, pp. 4096-4100.*
Rosin et al. Coevolutaion and subsite decomposition for the design of resistance-evading HIV-1 protease inhibitors. Journal of Molecular Biology 1999, vol. 287, p. 77-92.*
U.S. Appl. No. 09/580,491 Advisory Action dated Mar. 7, 2006, 2 pages.
U.S. Appl. No. 09/580,491 Final Office Action dated Aug. 26, 2003, 8 pages.

(Continued)

Primary Examiner — Louise Humphrey
(74) Attorney, Agent, or Firm — Woodcock Washburn LLP

(57) ABSTRACT

The invention provides novel mutations, mutation combinations or mutational profiles of HIV-1 reverse transcriptase and/or protease genes correlated with phenotypic resistance to HIV drugs. More particularly, the present invention relates to the use of genotypic characterization of a target population of HIV and the subsequent correlation of this information to phenotypic interpretation in order to correlate virus mutational profiles with drug resistance. The invention also relates to methods of utilizing the mutational profiles of the invention in databases, drug development, i.e., drug design, and drug modification, therapy and treatment design, clinical management and diagnostic analysis.

2 Claims, 2 Drawing Sheets

(56) References Cited

OTHER PUBLICATIONS

U.S. Appl. No. 09/580,491 Final Office Action dated Jan. 22, 2008, 7 pages.
U.S. Appl. No. 09/580,491 Final Office Action dated Sep. 12, 2005, 4 pages.
U.S. Appl. No. 09/580,491 Non-Final Office Action dated Dec. 16, 2004, 6 pages.
U.S. Appl. No. 09/580,491 Non-Final Office Action dated Dec. 23, 2002, 6 pages.
U.S. Appl. No. 09/580,491 Non-Final Office Action dated Dec. 4, 2001, 7 pages.
U.S. Appl. No. 09/580,491 Non-Final Office Action dated May 9, 2007, 5 pages.
U.S. Appl. No. 09/580,491 Non-Final Office Action dated Sep. 26, 2006, 3 pages.
U.S. Appl. No. 10/399,920 Final Office Action dated Aug. 4, 2006, 8 pages.
U.S. Appl. No. 10/399,920 Final Office Action dated May 2, 2007, 9 pages.
U.S. Appl. No. 10/399,920 Non-Final Office Action dated Aug. 25, 2005, 10 pages.
U.S. Appl. No. 10/518,525 Final Office Action dated Feb. 7, 2007, 6 pages.
U.S. Appl. No. 10/518,525 Final Office Action dated Oct. 18, 2007, 6 pages.
U.S. Appl. No. 10/518,525 Non-Final Office Action dated May 10, 2006, 8 pages.
U.S. Appl. No. 10/519,035 Non-Final Office Action dated Dec. 16, 2005, 8 pages.
U.S. Appl. No. 10/519,436 Final Office Action dated Mar. 4, 2009, 10 pages.
U.S. Appl. No. 10/519,436 Final Office Action dated Mar. 7, 2007, 10 pages.
U.S. Appl. No. 10/519,436 Final Office Action dated May 11, 2010, 9 pages.
U.S. Appl. No. 10/519,436 Final Office Action dated Oct. 18, 2007, 8 pages.
U.S. Appl. No. 10/519,436 Non-Final Office Action dated Jun. 30, 2008, 9 pages.
U.S. Appl. No. 10/519,436 Non-Final Office Action dated Mar. 13, 2006, 10 pages.
U.S. Appl. No. 10/519,436 Non-Final Office Action dated Sep. 17, 2009, 13 pages.
U.S. Appl. No. 11/613,584 Final Office Action dated Apr. 15, 2010, 11 pages.
U.S. Appl. No. 11/613,584 Non-Final Office Action dated Mar. 12, 2009, 8 pages.
U.S. Appl. No. 12/261,475 Non-Final Office Action dated May 4, 2010, 6 pages.
U.S. Appl. No. 12/261,475 Non-Final Office Action dated Oct. 18, 2010, 9 pages.
U.S. Appl. No. 12/352,626 Non-Final Office Action dated Jul. 23, 2010, 7 pages.
Abremski et al., "pol protein HIV-1," downloaded from <http://www.ncbi.nlm.nih.gov/protein/AAG03320> 2000: 1-2.
Angarano et al.; "Genotype and Phenotype Resistance: An Overview," *Journal of Biological Regulators and Homeostatic Agents*, 2000; 14:11-14.
Anton et al.; "Comparative Patterns of HIV-1 Genotypic and Phenotypic Resistance Profiles in Gut and Plasma," *3rd International Workshop on HIV Drug Resistance and Treatment Strategies*, 1999; Abstract 86, 4(1).
Bacheler et al.; "Genotypic Correlates of Phenotypic Resistance to Efavirenz in Virus Isolates from Patients Failing Nonnucleoside Reverse Transcriptase Inhibitor Therapy," *Journal of Virology*, 2001; 75(11):4999-5088.
Bacheler et al.; "Human Immunodeficiency Virus Type 1 Mutations Selected in Patients Failing Efavirenz Combination Therapy," *Antimicrobial Agents and Chemotherapy*, 2000; 44(9):2475-2484.

Bakhanashvili et al.; "Mutational studies of human immunodeficiency virus type 1 reverse transcriptase: the involvement of residues 183 and 184 in the fidelity of DNA synthesis," *FEBS Letters*, 1996; 391(3):257-262.
Bally, F. et al.; "Polymorphism of HIV Type 1 Gag p7/p1 and p1/p6 Cleavage Sites: Clinical Significance and Implications for Resistance to Protease Inhibitors," *AIDS Research and Human Retroviruses*, 2000; 16(13):1209-1213.
Balotta et al.; "Prevalence of Transmitted Nucleoside Analogue-Resistant HIV-1 Strains and Pre-Existing Mutations in *pol* Reverse Transcriptase and Protease Region: Outcome After Treatment in Recently Infected Individuals," *Antiviral Therapy*, 2000 5:7-14.
Been-Tiktak et al.; "In-Vitro Selection of HIV-1 Variants Resistant to Non-Nucleoside Reverse Transcriptase Inhibitors in Monocyte-Derived Macrophages," *Journal of Antimicrobial Chemotherapy*, 1997; 40:847-853.
Beerenwinkel et al.; "Diversity and Complexity of HIV-1 Drug Resistance: A Bioinformatics Approach to Predicting Phenotype from Genotype," *PNAS*, 2002; 99(2):8271-8276.
Bloor et al.; "Lamivudine-Resistant HIV-1 Clinical Isolates Lacking the Met184Val Mutation have Novel Polymorphisms in RT," *3rd International Workshop on HIV Drug Resistance and Treatment Strategies*, 1999; Abstract 25, 4(1).
Calvez, V.; "Resistance to Antiretroviral Drugs," *Antiviral Therapy*, 1998; 3(4):5-7.
Casado et al.; "Rate of Non-nucleoside Reverse Transcriptase Inhibitor Resistance Among Patients Failing a Nevirapine Plus Protease Inhibitor-Containing Regimen," *3rd International Workshop on HIV Drug Resistance and Treatment Strategies*, 1999; Abstract 114, 1(1).
Catucci et al.; "Development and Significance of the HIV-1 Reverse Transcriptase M184V Mutation During Combination Therapy with Lamivudine, Zidovudine, and Protease Inhibitors," *Journal of Acquired Immune Deficiency Syndromes*, 1999; 21:203-208.
Chen et al.; "Drug Resistance Mutations as Predictors of Phenotypic Zidovudine Resistance in HIV-1 infection," *AIDS*, 1997; 11(12):1528-1529.
Clevenbergh et al.; "Prevalence of Nonucleoside Reverse Transcriptase Inhibitor (NNRTI) Resistance-Associated Mutations and Polymorphisms in NNRTI-Naïve HIV-Infected Patients," *HIV Clin Trials*, 2002; 3(1):36-44.
Clotet et al.; "Efficacy and safety of darunavir-ritonavir at week 48 in treatment-experienced patients with HIV-1 infection in POWER 1 and 2: a pooled subgroup analysis of data from two randomised trials," *Lancet*, 2007; 369:1169-1178.
Coakley et al.; "Phenotypic and Genotypic Resistance Patterns of HIV-1 Isolates Derived from Individuals Treated with Didanosine and Stavudine," *AIDS*, 2000; 14:F9-F15.
Condra et al.; "Genotypic or phenotypic susceptibility testing may not predict clinical responses to indinavir," *1st International Workshop HIV Drug Resistance and Treatment Strategies and Eradication*, 1997; Abstract 47: 48-49.
Condra, Jon H.; "Resisting Resistance: Maximizing the Durability of Antiretroviral Therapy," *Annals of Internal Medicine*, 1998; 128(11):951-955.
Condra, Jon. et al.; "Genetic Correlates of In Vivo Viral Resistance to Indinavir, a Human Immunodeficiency Virus Type 1 Protease Inhibitor," *Journal of Virology*, 1996, 70(12):8270-8276.
Craig et al.; "HIV Protease Genotype and Viral Sensitivity to HIV Protease Inhibitors Following Saquinavir Therapy," *AIDS*, 1998; 12:1611-1618.
D'Aquila, R.; "HIV-1 Chemotherapy and Drug Resistance," *Clinical and Diagnostic Virology*, 1995; 3:299-316.
De Bethune et al.; "Does Natural or Acquired Resistance to Reverse Transcriptase and Protease Inhibitors, Observed in HIV-1 Groups M (Subtypes A-H) and O, Differ from Subtype B," *3rd International Workshop on HIV Drug Resistance and Treatment Strategies*, 1999; Abstract 49, 4(1).
De Oliveira, T. et al.; "Variability at Human Immunodeficiency Virus Type 1 Subtype C Protease Cleavage Sites: an Indication of Viral Fitness?," *Journal of Virology*, 2003; 77(17): 9422-9430.
Deeks et al.; "Correlation of Baseline Phenotypic Drug Susceptibility with 16 Week Virologic Response in a Pilot Combination Therapy Study in HIV-infected Patients who Failed Indinavir Therapy," *2nd*

(56) References Cited

OTHER PUBLICATIONS

*In'l Workshop on HIV Drug Resistance and Treatment Strategies*, Lake Maggiore, Italy, 1998; Abstract 53.
Deeks et al.; "Novel Four-Drug Salvage Treatment Regimens After Failure of a Human Immunodeficiency Virus Type 1 Protease Inhibitor-Containing Regimen: Antiviral Activity and Correlation of Baseline Phenotypic Drug Susceptibility with Virologic Outcome," *The Journal of Infectious Disease*, 1999; 179:1375-1381.
Descamps et al.; "Line Probe Assay for Detection of Human Immunodeficiency Virus type 1 Mutations Conferring Resistance to Nucleoside Inhibitors of Reverse Transcriptase: Comparison with Sequence Analysis," *Journal of Clinical Microbiology*, 1998; 36(7):2143-2145.
Descamps et al.; "Susceptibility of Human Immunodeficiency Virus Type 1 Group O Isolates to Antiretroviral Agents: In Vitro Phenotypic and Genotypic Analyses," *Journal of Virology*, 1997; 8893-8898.
Eastman et al.; "Comparison of Selective Polymerase Chain Reaction Primers and Differential Probe Hybridization of Polymerase Chain Reaction Products for Determination of Relative Amounts of Codon 215 Mutant and Wild-type HIV-1 Population," *Journal of Acquired Immune Deficiency Syndromes and Human Retrovirology*, 1995; 9:263-273.
Eastman, P. Scott, et al.; "Nonisotopic Hybridization Assay for Determination of Relative Amounts of Genotypic Human Immunodeficiency Virus Type 1 Zidovudine Resistance," *Journal of Clinical Microbiology*, 1995; 33(10):2777-2780.
Edelstein et al.; "Oligonucleotide Ligation Assay for Detecting Mutations in the Human Immunodeficiency Virus Type 1 *pol* Gene That are Associated with Resistance to Zidovudine, Didanosine, and Lamivudine," *Journal of Clinical Microbiology*, 1998; 569-572.
Eriksson, Bertil F.H. et al.; "Phosphorylation of 3'-Azido'2'3'-Dideoxyuridine and Preferential Inhibition of Human and Simian Immunodeficiency Virus Reverse Transcriptases by Its 5'-Triphosphate," *Antimicrobial Agents and Chemotherapy*, 1989; 33(10):1729-1734.
Eshleman et al.; "Analysis of Human Immunodeficiency Virus Type 1 Drug Resistance in Children Receiving Nucleoside Analogue Reverse-Transcriptase Inhibitors plus Nevirapine, Nelfinavir, or Ritonavir (Pediatric AIDS Clinical Trials Group 377)," *Journal of Infectious Disease*, 2001; 183:1732-1738.
Eshleman et al.; "HIV1 isolate 420111k042398 from USA pol protein (pol) gene," downloaded from <http://www.ncbi.nlm.nih.gov/nuccore/AF357746> 2002: 1-2.
Esté et al.; "HIV Phenotype & Genotype Data Highlights," *2nd International Workshop on HIV Drug Resistance and Treatment Strategies*, Lake Maggiore, Italy, 1998.
Fodor et al.; "DNA Sequencing: Massively Parallel Genomics," *Science*, 1997; 277:393-395.
Fodor, Stephen P.A. et al.; "Multiplexed Biochemical Assays With Biological Chips," *Nature*, 1993; 364:555-556.
Gianotti et al.; "Study on Mutations and Antiretroviral Therapy (SMART): Preliminary Results," *Antiviral Therapy*, 1999; 4(3):65-69.
Gianotti et al.; "The Rationale for a Study on HIV-1 Reverse Transcriptase Mutations and Outcome of Antiretroviral Therapy with Two Nucleoside Analogs," *Journal of biological Regulators and Homeostatic Agents*, 1999; 158-162.
Gingeras et al.; "Use of Self-Sustained Sequence Replication Amplification Reaction to Analyze and Detect Mutations in Zidovudine-Resistant Human Immunodeficiency Virus," *The Journal of Infectious Diseases*, 1991; 164:1066-1074.
Gonzales et al.; "pol polyprotein (HIV-1)," downloaded from <http://www.ncbi.nlm.nih.gov/protein/AAK35843 2001>: 1-3.
Gunthard et al.; "Human Immunodeficiency Virus Replication and Genotypic Resistance in Blood and Lymph Nodes After a Year of Potent Antiretroviral Therapy," *Journal of Virology*, 1998; 2422-2428.
Hammer et al.; "Relationship of Phenotypic and Genotypic Resistance Profiles to Virological Outcome in a Trial of Abacavir, Nelfinavir, Efavirenz and Adefovir Dipivoxil in Patients with Virological Failure Receiving Indinavir," *3rd International Workshop on HIV Drug Resistance and Treatment Strategies*, 1999; 4(1); Abstract 64.
Harada et al.; "Infection of HTLV-IIVLAV in HTLV-I-Carrying Cells MT-2 and MT-4 and Application in a Plaque Assay," *Science*, 1985; 229(4713):563-566.
Harrigan et al.; "Drug Resistance and Short Term Virological Response in Patients Prescribed Multidrug Rescue Therapy," *3rd International Workshop on HIV Drug Resistance and Treatment Strategies*, 1999; 4(1); Abstract 62.
Hertogs et al.; "A Blinded Comparative Analysis of Two Genotyping Service Laboratories: Full Sequence Analysis of HIV-1 Protease and Reverse Transcriptase," *3rd International Workshop on HIV Drug Resistance and Treatment Strategies*, 1999; 4(1); Abstract 87.
Hertogs et al.; "A Novel Human Immunodeficiency Virus Type 1 Reverse Transcriptase Mutational Pattern Confers Phenotypic Lamivudine Resistance in the Absence of Mutation 184V," *Antimicrobial Agents and Chemotherapy*, 2000; 44(3):568-573.
Hertogs et al.; "A Rapid Method for Simultaneous Detection of Phenotypic Resistance to Inhibitors of Protease and Reverse Transcriptase in Recombinant Human Immunodeficiency Virus Type 1 Isolates from Patients Treated with Antiretroviral Drugs," *Antimicrobial Agents and Chemotherapy*, 1998; 42(2):269-276.
Hertogs et al.; "Common, Rare and New Genotypic and/or Phenotypic HIV-1 Resistance Profiles Observed in Routine Clinical Practice: A Survey of Over 5000 Isolates," *3rd International Workshop on HIV Drug Resistance and Treatment Strategies*, 1999; 4(1); Abstract 108.
Hertogs et al.; "Comprehensive HIV Drug Resistance Monitoring Using Rapid, High-Throughput Phenotypic and Genotypic Assays with Correlative Data Analysis," *International Congress on Drug Therapy in HIV Infections*, 1998; 12(4):S11 (OP3.4).
Hertogs et al.; "Performance characteristics of phenotypic drug resistance testing (Antivirogram) in monitoring of anti-HIV therapy,"*International Workshop on HIV Drug Resistance, Treatment Strategies and Eradication*, 1997; St. Petersburg, Florida; Abstract 43.
Hertogs et al.; "Testing for HIV-1 Drug Resistance: New Developments and Clinical Implications," *Recent Res. Dev. Antimicrob. Agents Chemother.*, 1999; 3(Pt. 1):83-104.
Hertogs et al.; "The RT-Antivirogram™: a rapid and accurate method to determine phenotypic (multi)-drug resistance in plasma of patients treated with various HIV-1 RT inhibitors," *5th International Workshop on HIV Drug Resistance*, 1996; Whistler, Canada, Abstract 64.
Hirsch et al.; "Antiretroviral Drug Resistance Testing in Adults with HIV Infection," *JAMA*, 1998; 279(24):1984-1991.
Holodniy et al.; "Determination of Human Immunodeficiency Virus RNA in Plasma and Cellular Viral DNA Genotypic Zidovudine Resistance and Viral Load During Zidovudine-Didanosine Combination Therapy," *Journal of Virology*, 1995; 69(6):3510-3516.
Holodniy et al.; "Human Immunodeficiency Virus Reverse Transcriptase Codon 215 Mutations Diminish Virologic Response to Didanosine-Zidovudine Therapy in Subjects with Non-Syncytium-Inducing Phenotype," *The Journal of Infectious Diseases*, 1996; 174:854-857.
Hsu et al.; "Higher Fidelity of RNA-Dependent DNA Mispair Extension by M184V Drug-Resistant than Wild-type Reverse Transcriptase of Human Immunodeficiency Virus Type 1," *Nucleic Acids Research*, 1997; 25(22):4532-4536.
Ibanez et al.; "Human Immunodeficiency Virus Type 1 Population Bottleneck During Individual Therapy Causes a Genetic Drift in the Env Quasispecies," *Journal of General Virology*, 2000; 81:85-95.
International Search Report dated Apr. 12, 2008, for PCT/EP08/056356.
International Search Report dated Jan. 4, 2005 for PCT/EP03/050280.
International Search Report dated Jul. 17, 2003, for PCT/EP01/012338.
International Search Report dated Nov. 10, 2003, for PCT/EP03/50277.
International Search Report dated Oct. 22, 2003 for PCT/EP03/50279.

(56) References Cited

OTHER PUBLICATIONS

Iversen et al.; "Multidrug-Resistant Human Immunodeficiency Virus Type 1 Strains Resulting from Combination Antiretroviral Therapy," *Journal of Virology*; 1996; 70(2):1086-1090.

Ives et al.; "Emergence of Resistant Variants of HIV in vitro During Monotherapy with the Proteinase Inhibitor Saquinavir," *Journal of Antimicrobial Chemotherapy*, 1997; 39:771-779.

Japour et al.; "Standardized Peripheral Blood Mononuclear Cell Culture Assay for Determination of Drug Susceptibilities of Clinical Human Immunodeficiency Virus Type 1 Isolates," *Antimicrobial Agents Chemotherapy*, 1993; 37(5):1095-1101.

Kaufmann, G. R. et al.; "Impact of HIV Type 1 protease, Reverse Transcriptase, Cleavage Site, and p6 Mutations on the Virological Response to Quadruple Therapy with Saquinavir, Ritonavir, and Two Nucleoside Analogs," *AIDS Research and Human Retroviruses*, 2001; 17(6):487-497.

Kellam et al.; "Fifth Mutation in Human Immunodeficiency Virus Type 1 Reverse Transcriptase Contributes to the Development of High-Level Resistance to Zidovudine," *Proc. Natl. Acad. Sci. USA*; 1992; 89:1934-1938.

Kellam et al.; "Recombinant Virus Assay: A Rapid, Phenotypic Assay for Assessment of Drug Susceptibility of Human Immunodeficiency Virus Type 1 Isolates," *Antimicrobial Agents and Chemotherapy*, 1994; 38(1):23-30.

Kemp et al.; "A Novel Polymorphism at Codon 333 of Human Immunodeficiency Virus Type 1 Reverse Transcriptase Can Facilitate Dual Resistance to Zidovudine and L-2', 3'-Dideoxy-3'-Thiacytidine," *Journal of Virology*, 1998; 72:5093-5098.

Kemp et al.; "Analysis of 5000 HIV-1 Clinical Samples Reveals Complex Non-Nucleoside RT Inhibitor Resistance Patterns," *Antiviral Therapy*, 1999:4 (Suppl 1):20.

Kempf et al.; "Analysis of Virological Response to ABT-378/Ritonavir Therapy in Protease Inhibitor-Experienced Patients with Respect to Baseline Viral Phenotype and Genotype," $3^{rd}$ *International Workshop on HIV Drug Resistance and Treatment Strategies*, 1999; 4(1); Abstract 8.

Kim et al.; "Anti-HIV Type 1 Activity of 3'-Fluoro-3'-Deoxythymidine for Several Different Multidrug-Resistant Mutants," *Aids Research and Human Retroviruses*, 2001; 17(5):401-407.

Konig et al.; "Azidothymidine Triphosphate Is an Inhibitor of Both Human Immunodeficiency Virus Type 1 Reverse Transcriptase and DNA Polymerase Gamma," *Antimicrobial Agents and Chemotherapy*, 1989; 33(12):2109-2114.

Korber et al., "Numbering Positions in HIV Relative to HXB2CG," *Numbering Positions in HIV*, 1998; (III)102-111.

Kuritzkes, Daniel R.; "HIV Resistance to Current Therapies," *Antiviral Therapy*, 1997; 2(3);61-67.

Kusumi et al.; "Human Immunodeficiency Virus Type 1 Envelope Gene Structure and Diversity In Vivo and Cocultivation In Vitro," *Journal of Virology*, 1992; 66(2):875-885.

Larder et al.; "A Complete Survey in Over 1,500 Clinical HIV-1 Isolates, of Phenotypic and Genotypic Protease Inhibitor Resistance Profiles (Including Gag Cleavage Site Sequences) and Their Relation to Therapy History," *International Congress on Drug Therapy in HIV Infections*, 1998; 12(4):S11 Abstract Poster, OP3.5.

Larder et al.; "A Family of Insertion Mutations Between Codons 67 and 70 of Human Immunodeficiency Virus Type 1 Reverse Transcriptase Confer Multinucleoside Analog Resistance," *Antimicrob. Agents Chemother.*, 1999; 43(8):1961-1967.

Larder et al.; "HIV with Reduced Sensitivity to Zidovudine (AZT) Isolated During Prolonged Therapy," *Reports*, 1989; 243:1731-1734.

Larder et al.; "Multi-nucleoside drug resistance is conferred by a family of insertion mutations in HIV-1 reverse transcriptase," *Interscience Conference on Antimicrobial Agents and Chemotherapies*, 1998; 38:28 (Abstract No. LB-4).

Larder et al.; "Multiple Mutations in HIV-1 Reverse Transcriptase Confer High-Level Resistance to Zidovudine (AZI)," *Science*, 1989; 246(4934):1155-1158.

Larder et al.; "Predicting HIV-1 Phenotypic Resistance from Genotype Using a Large Phenotype-Genotype Relational Database," $3^{rd}$ *International Workshop on HIV Drug Resistance and Treatment Strategies*, 1999; 4(1); Abstract 59.

Larder et al.; "Tipranavir Inhibits Broadly Protease Inhibitor-Resistant HIV-1 Clinical Samples," *AIDS*, 2000; 14:1943-1948.

Larder et al.; "Tipranavir is Active Against a Large Selection of Highly Protease Inhibitor-Resistance HIV-1 Clinical Samples," $3^{rd}$ *International Workshop on HIV Drug Resistance and Treatment Strategies*, 1999; 4(1); Abstract 5.

Larder et al.; "Zidovudine Resistance Predicted by Direct Detection of Mutations in DNA from HIV-Infected Lymphocytes," *AIDS*, 1991; 5:137-144.

Leigh-Brown et al.; "Associations Between Amino Acids in the Evolution of HIV Type 1 Protease Sequences Under Indinavir Therapy," *AIDS Research and Human Retroviruses*, 1999; 15(3):247-253.

Lennerstrand et al.; "Mechanism of Zidovudine and Stavudine Resistance for HIV-1 RT with Amino Acid Insertions Between Codons 68 and 70," $3^{rd}$ *International Workshop on HIV Drug Resistance and Treatment Strategies*, 1999; 4(1); Abstract 32.

Lennerstrand, J. et al.; "A Method for Combined Immunoaffinity Purification and Assay of HIV-1 Reverse Transcriptase Activity Useful for Crude Samples," *Analytical Biochemistry*, 1996; 235(2):141-152.

Leriche-Guerin et al.; "Correlation Between Antiretroviral Resistance Mutations, Biological Parameters, and Clinical Evolution in Zidovudine-Treated Patients Infected with Human Immunodeficiency Virus Type 1," *Eur. J. Clin. Microbiol. Infect. Dis.*, 1997; 16:660-668.

Lorenzi et al.; "Impact of Drug Resistance Mutations on Virologic Response to Salvage Therapy," *AIDS*, 1999; 13:F17-F21.

Margot et al.; "Genotypic and Phenotypic Analyses of HIV-1 in Antiretroviral-Experienced Patients Treated with Tenofovir DF," *AIDS*, 2002; 16:1227-1235.

Martinez et al.; "protease (HIV-1)," downloaded from <http://www.ncbi.nlm.nih.gov/protein/AAF29689> 2000.

Matayoshi et al.; "Novel Flurogenic Substrates for Assaying Retroviral Proteases by Resonance Energy Transfer," *Science*, 1990; 247:954-958.

Mellors et al.; "Mutations in HIV-1 Reverse Transcriptase and Protease Associated with Drug Resistance," *Mutations in RT and Protease*, 1995; III-93-III-105.

Miller et al.; "Correlates of Resistance to Individual Nucleoside Drugs in Patients Who Have Never Taken Them," $3^{rd}$ *International Workshop on HIV Drug Resistance and Treatment Strategies*, 1999; 4(1); Abstract 41.

Miller et al.; "Patterns of Resistance and Cross-Resistance to Human Immunodeficiency Virus Type 1 Reverse Transcriptase Inhibitors in Patients Treated with the Nonnucleoside Reverse Transcriptase Inhibitor Loviride," *Antimicrobial Agents and Chemotherapy*, 1998; 42(12):3123-3129.

Miller et al.; "Phenotypic Susceptibility to Adefovir Dipivoxil in Clinical Samples with Defined RT Genotypic Resistance Patterns," $3^{rd}$ *International Workshop on HIV Drug Resistance and Treatment Strategies*, 1999; 4(1); Abstract 40.

Miller et al.; "Prevalence of Baseline Drug Resistance Mutations in Primary HIV Infection Patients from the QUEST Study," $3^{rd}$ *International Workshop on HIV Drug Resistance and Treatment Strategies*, 1999; 4(1); Abstract 141.

Mohamed et al.; "The Sequential Occurrence of *pol* 215 and *pol* 41 Zidovudine Resistance Mutations is Associated in an Additive Fashion with Low CD4 Cell Counts and High Plasma and Cellular HIV Viral Load," *Antiviral Research*, 1998; 39:47-53.

Moyle, G.; "Current knowledge of HIV-1 Reverse Transcriptase Mutations Selected During Nucleoside Analogue Therapy: The Potential to Use Resistance Data to Guide Clinical Decisions," *Journal of Antimicrobial Chemotherapy*, 1997; 40:765-777.

Moyle, G.; "Viral Resistance Patterns Selected by Antiretroviral Drugs and Their Potential to Guide Treatment Choice," *Exp. Opin. Invest. Drugs*, 1997; 6(8):943-964.

(56) References Cited

OTHER PUBLICATIONS

Nakano et al.; "Clonal Selection of HIV Type 1 Variants Associated with Resistance to Foscarnet in Vitro: Confirmation by Molecular Evolutionary Analysis," *Aids Research and Human Retroviruses*, 1997; 13(7):563-573.
Parikh et al.; "Mutations in Retroviral Genes Associated with Drug Resistance," *HIV Database Review*, 2000; 106-161.
Patick et al.; "Antiviral and Resistance Studies of AG1343, an orally Bioavailable Inhibitor of Human Immunodeficiency Virus Protease," *Antimicrobial Agents and Chemotherapy*; 1996; 40(2):292-297.
Paulous et al.; "A 1 Week, Single-Cycle Protease Inhibitor Resistance Assay," *International Workshop on HIV Drug Resistance, Treatment Strategies and Eradication Session 3*, 1997; Abstract 46.
Pauwels et al.; "A Comprehensive HIV Drug Resistance Monitoring Using Rapid, High-Throughput Phenotypic and Genotypic Assays with Correlative Data Analysis," $2^{nd}$ *Annual Workshop on HIV Drug Resistance and Treatment Strategies*, Lake Maggiore, Italy, 1998; Abstract 51.
Pauwels et al.; "Rapid and Automated Tetrazolium-based Colorimetric Assay for the Detection of Anti-HIV Compounds," *Journal of Virological Methods*, 1988; 20(4):309-321.
Perez-Olmeda et al.; "Usefulness of Genotypic Analysis of Resistance to Nucleoside Analogues in the Clinical Setting," *Eur. J. Clin. Microbrial Infect. Dis.*, 1999; 18:448-449.
Piketty et al., "Efficacy of a Five-Drug Combination Including Ritonavir, Saquinavir and Efavirenz in Patients Who Failed on a Conventional Triple-Drug Regimen: Phenotypic Resistance to Protease Inhibitors Predicts Outcome of Therapy," *AIDS*, 1999; 13:F71-F77.
Proudfoot et al., "Novel Non-nucleoside Inhibitors of Human Immunodeficiency Virus Type 1 (HIV-1) Reserve Transcriptase. 4.1 2-Substituted Dipyridodiazepinones as Potent Inhibitors of Both Wild-Type and Cysteine-181 HIV-1 Reverse Transcriptase Enzymes," *Journal of Medical Chemistry*, 1995; 38(24):4830-4838.
Ren et al.; "Crystal Structures of HIV-1 RT Inhibitor Complexes: 'Second Generation' NNRTIs, Efavirenz and S-1153 (AG1549), and NNRTI- and NRTI-resistant Mutant Forms," $3^{rd}$ *International Workshop on HIV Drug Resistance and Treatment Strategies*, 1999; 4(1); Abstract 20.
Richman et al.; "Detection of Mutations Associated with Zidovudine Resistance in Human Immunodeficiency Virus by use of the Polymerase Chain Reaction," *Journal of Infectious Diseases*, 1991; 164:1075-1081.
Richman et al.; "Nevirapine Resistance Mutations of Human Immunodeficiency Virus Type 1 Selected during Therapy," *Journal of Virology*, 1994; 68(3):1660-1666.
Robinson et al.; "HIV Type 1 Protease Cleavage Site Mutations and Viral Fitness: Implications for Drug Susceptibility Phenotyping Assays," *AIDS Research and Human Retroviruses*, 2000; 16(12):1149-1156.
Rusconi, Stefano et al.; "Susceptibility to PNU-140690 (Tipranavir) of Human: Immunodeficiency Virus Type 1 Isolates Derived from Patients with Multidrug Resistance to Other Protease Inhibitors," *Antimicrobial Agents and Chemotherapy*, 2000; 44(5):1328-1332.
Saag et al.; "A Short-Term Clinical Evaluation of L-697,661, a Non-Nucleoside Inhibitor of HIV-1 Reverse Transcriptase," *The New England Journal of Medicine*; 1993; 329:1065-1072.
Schapiro et al.; "Clinical Cross-Resistance Between the HIV-1 Protease Inhibitors Saquinavir and Indinavir and Correlations with Genotypic Mutations," *AIDS*, 1999; 13:359-365.
Schinazi et al., "Mutations in Retroviral Genes Associated with Drug Resistance: 2000-2001 Update," *International Antiviral News*, 2000; 8(5):65-91.
Schinazi et al.; "Mutations in Retroviral Genes Associated with Drug Resistance," *International Antiviral News*, 1997; 5:129-142.
Schmidt et al.; "HIV-1 isolate 992286 from Germany pol protein (pol) gene," downloaded from <http://www.ncbi.nlm.nih.gov/nucleotide/AF347471>, 2002: 1-2.
Schmidt et al.; "pol protein (HIV-1)," downloaded from <http://www.ncbi.nlm.nih.gov/protein/AAK32676>, 2002: 1-2.

Schmidt et al.; "Simple Algorithm Derived from a Geno-/Phenotypic Database to Predict HIV-1 Protease Inhibitor Resistance," *AIDS*, 2000; 14:1731-1738.
Schmit et al.; "Recent Advances in Antiretroviral Therapy and HIV Infection Monitoring"; *Intervirology*, 1997; 40:304-321.
Schmit et al.; "Resistance-related Mutations in the HIV-1 Protease Gene of Patients Treated in 1 Year with the Protease Inhibitor Ritonavir (ABT-538)," *AIDS*, 1996; 10:995-999.
Seki et al.; "Isolation and characterization of human immunodeficiency virus type-1 mutants resistant to the non-nucleotide reverse transcriptase inhibitor MKC-442," *Antiviral Chemistry & Chemotherapy*, 1995; 6(2):73-79.
Servais et al.; "Comparison of DNA Sequencing and a Line Probe Assay for Detection of Human Immunodeficiency Virus Type 1 Drug Resistance Mutations in Patients Failing Highly Active Antiretroviral Therapy," *Journal of Clinical Microbiology*, 2001; 39(2):454-459.
Servais et al.; "Genotypic Correlates of Resistance to HIV-1 Protease Inhibitors on Longitudinal Data: The Role of Secondary Mutations," *Antiviral Therapy*, 2002; 6:239-248.
Servais, J.A.; "V-1 Reverse Transcriptase (human immunodeficiency virus 1), Accession No. CAB86592," downloaded from http://www/ncbi.nlm.nih.gov/entrez/viewer.fcgi?db=protein&val=7529531, 2006.
Shafer et al.; "Highly Active Antiretroviral Therapy for the Treatment of Infection with Human Immunodeficiency Virus Type 1," *Biomedicine & Pharmacotherapy*, 1999; 53:73-86.
Shafer et al.; "HIV-1 isolate PCCPROT48 from USA, protease (pol) gene," downloaded from <http://www.ncbi.nlm.nih.gov/nucleotide/AF085133>, 2001.
Shafer et al.; "Human Immunodeficiency Virus Reverse Transcriptase and Protease Sequence Database," *Nucleic Acids Research*, 1999; 27(1):348-352.
Shafer et al.; "Human Immunodeficiency Virus Reverse Transcriptase and Protease Sequence Database," *Nucleic Acids Research*, 2000; 28(1):346-348.
Shafer et al.; "Online Comparison of HIV-1 Drug Resistance Algorithms Identifies Rates and Causes of Discordant Interpretations," *Antiviral Therapy*, 2001; 6(Supplement 1):101-102.
Stein et al.; "Sequence Analysis of Proviral HIV RT Amplified Directly by a Semi-Quantitative Technique from AZT Treated Patients," *Journal of Medical Virology*, 1994; 44:115-121.
Stuyver et al.; "Line Probe Assay for Rapid Detection of Drug-Selected Mutations in the Human Immunodeficiency Virus Type 1 Reverse Transcriptase Gene," *Antimicrobial Agents and Chemotherapy*, 1997; 41(2):284-291.
Tamalet et al.; "Multidrug Resistance Genotypes (Insertions in the β3-β4 Finger Subdomain and MDR Mutations) of HIV-1 Reverse Transcriptase from Extensively Treated Patients: Incidence and Association with Other Resistance Mutations," *Virology*, 2000; 270:310-316.
Toth et al.; "A simple, continuous flurometric assay for HIV protease," *Int. J. Peptide Protein Res,* 1990: 544-550.
Tyagi et al.; "Continuous Assay of the Hydrolytic Activity of Human Immunodeficiency Virus-1 Protease," *Analytical Biochemistry*; 1992: 143-148.
Tyagi et al.; "Multicolor molecular beacons for allele discrimination," *Nature Biotechnology*, 1998: 49-50.
Vandamme et al.; "Managing Resistance to Anti-HIV Drugs," *Drugs*, 1999; 337-361.
Vasudevachari, M.D. et al.; "Emergence of Protease Inhibitor Resistance Mutations in Human Immunodeficiency Virus Type 1 Isolates from Patients and Rapid Screening Procedure for Their Detection," *Antimicrobial Agents and Chemotherapy*, 1996; 40(11):2535-2541.
Vella, S.; "Advances in the Virology of HIV Infection and Implications for Clinical Management," *Aids Clinical Care*, 1998; 10(3):17-19.
Verbiest et al.; "An Epidemiological Prospective Survey Assessing the Prevalence of HIV-1 Drug Resistance in 230 HIV-1-Positive Antiretroviral-Naïve Patients from the USA," $3^{rd}$ *International Workshop on HIV Drug Resistance and Treatment Strategies*, 1999; 4(1); Abstract 122.
Vergne et al., "POL precursor (HIV-1)" downloaded from http://www.ncbi.nlm.nih.gov/protein/CAC03089, 2000: 1-2.

(56) References Cited

OTHER PUBLICATIONS

Vergne et al.; "Genetic Diversity of Protease and Reverse Transcriptase Sequences in Non-Subtype-B Human Immunodeficiency Virus Type 1 Strains: Evidence of Many Minor Drug Resistance Mutations in Treatment-Naïve Patents," *Journal of Clinical Microbiology*, 2000; 38(11):3919-3925.

Verheyen, J. et al.; "Compensatory mutations at the HIV cleavage sites p7/p1 and p1/p6-gag in therapy—naive and therapy-experienced patients," *Antiviral Therapy*, 2006; 11(7): 879-887.

Villahermosa et al.; "Evaluation of Mixtures of Wild-Type HIV-1 and HIV-1 with Resistance Point Mutations Against Reverse Transcriptase Inhibitors," *Antiviral Therapy*, 1998; 3:221-227.

Vingerhoets et al.; "The Accuracy and Reproducibility of High Throughput Genotypic and Phenotypic HIV-1 Resistance Testing Under EN45001 and CLIA Accreditation Labels," $3^{rd}$ *International Workshop on HIV Drug Resistance and Treatment Strategies*, 1999; 4(1); Abstract 77.

Walter et al.; "Rapid, Phenotypic HIV-1 Drug Sensitivity Assay for Protease and Reverse Transcriptase Inhibitors," *Journal of Clinical Virology*, 1999; 13:71-80.

Wang et al.; "Design and Synthesis of New Fluorogenic HIV Protease Substrates Based on Resonance Energy Transfer," *Tetrahedron Letters*, 1990: 6493-6496.

Watkins et al.; "Protease HIV1," downloaded from http://www.ncbi.nlm.nih.gov/protein/Q7ZCQ9, 2000.

Watkins et al.; "Selection of High-Level Resistance to Human Immunodeficiency Virus Type 1 Protease Inhibitors," *Antimicrobial Agents and Chemotherapy*, 2003; 47(2):759-769.

Weber et al.; "Molecular Mechanics Analysis of Drug-Resistant Mutants of HIV Protease," *Protein Engineering*, 1999; 12(6);469-474.

Wegner et al.; "High Frequency of Antiretroviral Drug Resistance in HIV-1 From Recently Infected Therapy-Naïve Individuals," $3^{rd}$ *International Workshop on HIV Drug Resistance and Treatment Strategies*, 1999; 4(1); Abstract 119.

Wegner et al.; "Prevalence of Genotypic and Phenotypic Resistance to Anti-Retroviral Drugs in a Cohort of Therapy-Naïve HIV-1 Infected US Military Personnel," *AIDS*, 2000; 14:1009-1015.

Wegner et al.; "The Potential Role of Resistance Testing and Therapeutic Drug Monitoring in the Optimization of Antiretroviral Drug Therapy," $3^{rd}$ *International Workshop on HIV Drug Resistance and Treatment Strategies*, 1999; 4(1); Abstract 112.

Winters et al.; "Human Immunodeficiency Virus Type 1 Reverse Transcriptase Genotype and Drug Susceptibility Changes in Infected Individuals Receiving Dideoxyinosine Monotherapy for 1 to 2 Years," *Antimicrobial Agents and Chemotherapy*, 1997; 41(4): 757-762.

Yahi et al.; "Mutation Patterns of the Reverse Transcriptase and Protease Genes in Human Immunodeficiency Virus Type 1-Infected Patients Undergoing Combination Therapy: Survey of 787 Sequences," *Journal of Clinical Microbiology*, 1999; 37(12): 4099-4106.

Yee et al.; "Prospects for Gene Therapy Using HIV-Based Vectors," *Somatic Cell and Molecular Genetics*, 2001; 26:(1-6):159-174.

Yin et al.; "Overcoming HIV drug resistance through rational drug design based on molecular, biochemical, and structural profiles of HIV resistance," *Cellular Molecular Life Sciences*, 2006, 63:1706-1724.

Zhang Y-M, et al.; "Drug Resistance during Indinavir Therapy Is Caused by Mutations in the Protease Gene and in Its Gag Substrate Cleavage Sites," *Journal of Virology*, 1997; 71(9): 6662-6670.

Zolopa et al.; "A Comparison of Phenotypic, Genotypic and Clinical/Treatment History Predictors of Virological Response to Saquinavir/Ritonavir Salvage Therapy in a Clinic-based Cohort," $3^{rd}$ *International Workshop on HIV Drug Resistance and Treatment Strategies*, 1999; 4(1); Abstract 68.

Zolopa et al.; "HIV-1 Genotypic Resistance Patterns Predict Response to Saquinavir-Ritonavir Therapy in Patients in Whom Previous Protease Inhibitor Therapy Had Failed," *Annals of Internal Medicine*, 1999; 131(11): 813-821.

Hertogs et al., "Phenotypic and genotypic analysis of clinical HIV-1 isolates reveals extensive protease inhibitor cross-resistance: a survey of over 6000 samples", AIDS, 14, 2000, 1203-1210.

\* cited by examiner

MUTATIONAL PROFILES IN HIV-1 REVERSE TRANSCRIPTASE CORRELATED WITH PHENOTYPIC DRUG RESISTANCE

CROSS REFERENCE TO THE RELATED APPLICATIONS

This application is a continuation of U.S. application Ser. No. 10/399,920 filed Apr. 16, 2003 (now abandoned), which represents entry into the U.S. National Stage of PCT/EP01/12338, filed Oct. 22, 2001, and which in turn claims priority of U.S. Provisional Application Ser. No. 60/241,801 and U.S. Provisional Application Ser. No. 60/241,844, both filed Oct. 20, 2000. The complete disclosures of the aforementioned related U.S. patent application is hereby incorporated herein by reference for all purposes.

The present invention is directed to the field of nucleic acid diagnostics and the identification of base variation in target nucleic acid sequences. More particularly, the present invention relates to the use of such genotypic characterization of a target population of HIV and the subsequent association, i.e., correlation, of this information to phenotypic interpretation in order to correlate virus mutational profiles with drug resistance. The invention also relates to methods of utilizing the mutational profiles of the invention in drug development, i.e., drug design, drug modification, and drug development, therapy and treatment design, clinical management and diagnostic analysis.

Retroviral inhibitors may block viral replication in various ways. For example, Nucleoside Reverse Transcriptase Inhibitors (NRTIs), compete with the natural nucleoside triphosphates for incorporation into elongating viral DNA by reverse transcriptase. Chemical modifications that distinguish these compounds from natural nucleosides result in DNA chain termination events. NRTIs that are currently available include zidovudine (ZDV), didanosine (ddl), zalcitabine (ddC), stavudine (d4T), lamivudine (3TC) and abacavir (ABC).

Nucleotide reverse transcriptase inhibitors (NtRTIs) have the same mode of action as NRTIs, but they differ in that they are already monophosphorylated and therefore they require fewer metabolic steps. Adefovir (bis-POM-PMEA) and bis-POC PMPA belong to this category of treatments.

Non-Nucleoside Reverse Transcriptase inhibitor (NNRTIs) are a group of structurally diverse compounds which inhibit HIV reverse transcriptase by noncompetitive binding to or close to the active site of the viral reverse transcriptase enzyme, thereby inhibiting its activity. Available compounds in this group include nevirapine (NVP), delavirdine (DLV) and efavirenz.

Protease Inhibitors (PIs) are peptidomimetic and bind to the active site of the viral protease enzyme, thereby inhibiting the cleavage of precursor polyproteins necessary to produce the structural and enzymatic components of infectious virions. PIs that are currently available include saquinavir (SQV), ritonavir (RTV), indinavir (IDV) nelfinavir (NFV), amprenavir (APV) and ABT-378 (lopinavir).

The options for antiretroviral therapy have improved considerably as new agents have become available. Current guidelines for antiretroviral therapy recommend a triple combination therapy regimen for initial treatment, such as one PI and 2 NRTIs or one NNRTI and 2 NRTIs. These combination regimens show potent antiretroviral activity and are referred to as HAART (highly active antiviral therapy).

Additionally, the development and standardization of plasma HIV-1 RNA quantification assays has led to the use of viral load measurements as a key therapy response monitoring tool. The goal of antiretroviral therapy is to reduce plasma viremia to below the limit of detection on a long-term basis. However, in a significant number of patients, maximal suppression of virus replication is not achieved and for those in whom this goal is reached, a significant number experience viral load rebound. Viral load data provide no information on the cause of the failure.

Why therapies fail may be due to a number of factors, including insufficient antiviral activity of the regimen, individual variations in drug metabolism and pharmacodynamics, difficulties in adhering to dosing regimen, requirements for treatment interruption due to toxicity, and viral drug resistance. Moreover, drug resistance may develop in a patient treated with sub-optimal antiretroviral therapy or a patient may be infected with drug-resistant HIV-1. Although drug resistance may not be the primary reason for therapy failure, in many cases any situation which permits viral replication in the presence of an inhibitor sets the stage for selection of resistant variants.

Viral drug resistance can be defined as any change in the virus that improves replication in the presence of an inhibitor. HIV-1 drug resistance was first described in 1989 and involved patients that had been treated with zidovudine monotherapy, which represented the only treatment option at that time. See Larder, B. A., et al., *Science* 243, 1731-1734 (1989). Emergence of resistance is almost always being observed during the course of treatment of patients with single antiretroviral drugs. Similarly, in vitro passage of viral cultures through several rounds of replication in the presence of antiretroviral compounds leads to the selection of viruses whose replication cycle is no longer susceptible to the compounds used. Resistance development has also been observed with the introduction of dual NRTI combination therapy as well as during the administering of the more potent NNRTIs and PIs. Individual antiretroviral agents differ in the rate at which resistance develops: selection for resistant variants may occur within weeks of treatment or resistance may emerge after a longer treatment period.

Extensive genetic analysis of resistant viral isolates generated through in vivo or in vitro selection has revealed that resistance is generally caused by mutations altering the nucleotide sequence at some specific site(s) of the viral genome. The mutational patterns that have been observed and reported for HIV-1 and that are correlated with drug resistance are very diverse: some antiretroviral agents require only one single genetic change, while others require multiple mutations for resistance to appear. A summary of mutations in the HIV genome correlated with drug resistance has been compiled. See Schinazi, R. F., Larder, B. A. & Meliors, J. W. 1997. *Int. Antiviral News.* 5, 129-142 (1997). Additionally, an electronic listing with mutations has also become available from the internet, such as from the websites of the HIV Databases (hiv-web.lanl.gov), the Stanford University HIV Drug Resistance Database (hivdb.stanford.edu), and the HIVresistanceWeb (hivresistanceweb.com).

It should be noted that the degree of susceptibility of a genetic variant to an antiretroviral compound is expressed herein relative to the wild-type virus (HIV III/B/LAI reference sequence) as found, for example, in GenBank (accession number K03455, SEQ ID NO:1), the sequence of which is hereby incorporated by reference. Susceptibilities are generally expressed as ratios of $IC_{50}$ or $IC_{90}$ values (the $IC_{50}$ or $IC_{90}$ value being the drug concentration at which 50% or 90% respectively of the viral population is inhibited from replicating). Additionally, the genetic mutation is normally written as in reference to the wild type virus, i.e., K101N refers to replacement of a Lysine at codon 101 with a Asparagine. However, the mutations of the invention do not depend on the wild-type example listed in order to be within the practice of the invention. For example, the mutation 101N, refers to an Asparagine at the 101 codon regardless of whether there was a Lysine at 101 prior to mutation.

Of course, as antiretroviral drugs are administered for longer periods of time, mostly in combination with each other, and as new antiretrovirals are being developed and added to the present drugs, new resistance-correlated genetic variants are being discovered. Of particular import is that the combination of antiretroviral agents can influence resistance characteristics. For example, different NNRTI resistance-correlated mutations were selected on NNRTI-zidovudine combination therapy and different NRTI resistance-correlated mutations were selected in dual NRTI combination therapy. In the latter case, the result is high-level multi-drug resistance to all NRTIs.

Moreover, once viral resistance has developed, salvage therapy options may be severely restricted due to cross-resistance within each drug class. Recently, interest has been focused on the characterization of alterations in viral drug susceptibility for better clinical management. This is as important for initial treatment as for when a therapy change is called for in order to minimize the emergence of resistance and improve the long-term prognosis of the patient. The choice of therapy regimen will be supported by knowledge of the resistance profile of the circulating virus population. Additionally, therapy combinations will have a greater chance of being effective if they include agents that have a demonstrated potential of suppressing a particular virus population.

To achieve these and other advantages, and in accordance with the purpose of the invention as embodied and broadly described herein, the present invention, in one aspect, provides a computer system comprising a database correlating the presence of at least one mutation in an HIV reverse transcriptase and the resistance of at least one strain of HIV to a reverse transcriptase inhibitor (RTI); and/or a database correlating the presence of at least one mutation in an HIV protease and the resistance of at least one strain of HIV to a protease inhibitor (PI). More specifically, the database comprises a set of records corresponding to a correlation between a mutation and drug resistance.

In a further embodiment, the invention provides for a method of identifying drugs effective against NNRTI or NRTI resistant strains of HIV, the method comprising the steps of: providing at least one strain of HIV comprising HIV reverse transcriptase containing at least one mutation described herein, determining the phenotypic response of the drug to the strain of HIV, and using the phenotypic response to determine the effectiveness of the drug. In an even further embodiment, the invention provides a method of identifying drugs effective against protease inhibitor (PI) resistant strains of HIV, wherein the strain of HIV comprises HIV protease containing at least one mutation described herein, determining the phenotypic response of said drug to said strain of HIV, and using the phenotypic response to determine the effectiveness of the drug. In another embodiment, the invention provides for the drug identified using the methods of the invention.

The invention also provides for a method of designing therapy for treating patients infected with HIV comprising: collecting a sample from an HIV-infected patient; determining whether the sample comprises at least one nucleic acid encoding HIV reverse transcriptase having at least one mutation described herein or HIV protease having at least one mutation described herein; and using the presence of the nucleic acid to design a therapy for the patient.

The invention also includes isolated HIV reverse transcriptase complexes resistant to at least one NNRTI or at least one NRTI comprising at least one mutation described above and an isolated HIV protease complex resistant to a PI comprising at least one mutation described above.

It is to be understood that both the foregoing general description and the following detailed description are exemplary and explanatory only and are not restrictive of the invention as claimed.

DETAILED DESCRIPTION OF THE INVENTION

Figure 1A:
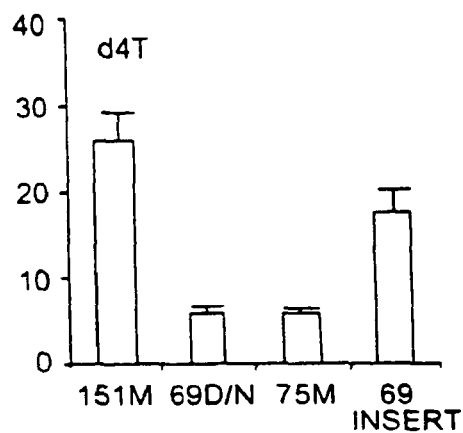
FIG. 1: Nucleoside analogue susceptibility of MDIR patient-derived recombinant HIV variants. Recombinant viruses were produced from patient plasma samples as described in Example 2 and tested for susceptibility to (a) d4T, (b) ddC and (c) ddI. The mean fold increase in $IC_{50}$ values (Mean fold resistance) relative to wild-type controls are shown for groups of viruses with different genotypes, i.e., the codon 151-M multi-drug resistance cluster (n=27), viruses with 69D/N (n=195), or 75M (n=43) in a background of AZT and 3TC resistance mutations and codon 69 insertion mutants (n=45) in a background of AZT resistance mutations. Error bars indicate standard errors. Note that the total number (n=310) is higher than the 302 MDR samples described because a small minority were 69D/N and 75M double mutants and are represented in both groups.
Figure 1B:
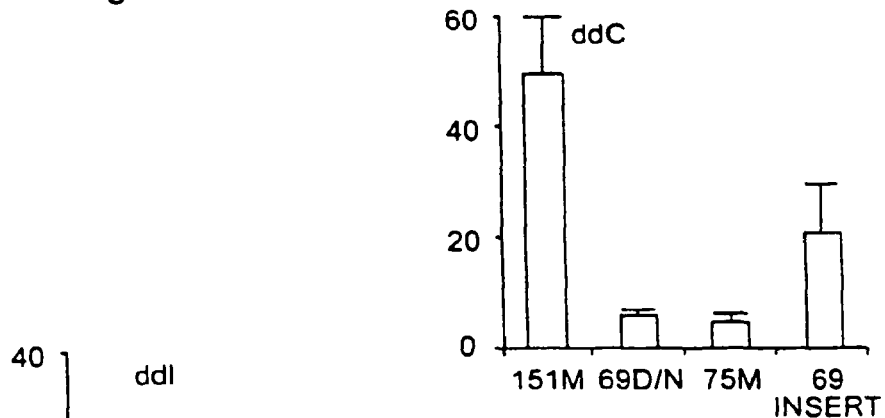
Figure 1C:
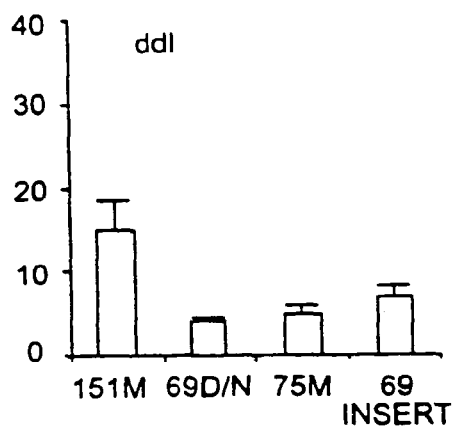

The invention, in one aspect, provides novel mutations or mutational profiles of HIV-1 reverse transcriptase and/or protease genes correlated with phenotypic resistance to anti-HIV drugs. More particularly, the present invention also relates to the use of genotypic characterization of a target population of HIV and the subsequent correlation of this information to phenotypic interpretation in order to correlate virus mutational profiles with drug resistance. The invention also relates to methods of utilizing the mutational profiles of the invention in databases, drug development, i.e., drug design, and drug modification, therapy and treatment design, clinical management and diagnostic analysis.

The present invention concerns a computer system comprising:

at least one database correlating the presence of at least one mutation in a human immunodeficiency virus (HIV) reverse transcriptase and resistance of at least one strain of HIV to a reverse transcriptase inhibitor, comprising:

at least one set of records corresponding to a correlation between at least one mutation chosen from 44D, 77L, 115F, 118I, 184V, 208Y, 210W, 211K, 214F, 215F, 215Y, 219E, 219N, and 219Q, and resistance to d4T, a record corresponding to a correlation between mutation 184I and resistance towards lamivudine, at least one set of records corresponding to a correlation between at least one mutation chosen from 115F and 184V and resistance towards abacavir.

a combination of 62V, 75T, 77L, 116Y and 151M and resistance towards all nucleoside analogues at least one set of records corresponding to a correlation between at least one mutation chosen from 101H, 101P, 103H, 103S, 103T, 106M, 181S, and 190Q and resistance towards nevirapine, at least one set of records corresponding to a correlation between at least one mutation chosen from 101H, 101P, 103H, 103N, 103S, 103T, 106M, 181C, 181S, 190Q and 236L and resistance towards delavirdine, at least one set of records corresponding to a correlation between at least one mutation chosen from 101H, 101P, 103H, 103S, 103T, 106M, 181S, 190Q and 236L and resistance towards efavirenz, a combination of 184V and 41L and 215Y, wherein the 184V resistance mutation reverses the effect of 41L and 215Y mutations on zidovudine a 236L mutation, which increases the sensitivity towards nevirapine at least one database correlating the presence of at least one mutation in a human immunodeficiency virus (HIV) protease and resistance of at least one strain of HIV to a protease inhibitor, comprising:

at least one set of records corresponding to a correlation between at least mutation selected from 54L, 54M, 54V, 84A, 84C and 84L and resistance towards a protease inhibitors selected from amprenavir, saquinavir, nelfinavir, ritonavir, indinavir.

The present invention further concerns a method of evaluating the effectiveness of an antiviral therapy of an HIV-infected patient comprising:

(a) collecting a sample from an HIV-infected patient;

(b) determining whether the sample comprises at least one nucleic acid encoding HIV having at least one mutation selected from:

i) a first nucleic acid encoding a HIV reverse transcriptase having at least one mutation chosen from 44D, 77L, 115F, 118I, 184V, 208Y, 210W, 211K, 214F, 215F, 215Y, 219E, 219N, and 219Q, and resistance to d4T, 184I and resistance towards lamivudine, 115F and 184V and resistance towards abacavir.

62V, 75T, 77L, 116Y and 151M and resistance towards all nucleoside analogues 101H, 101P, 103H, 103S, 103T, 106M, 181S, and 190Q and resistance towards nevirapine, 101H, 101P, 103H, 103N, 103S, 103T, 106M, 181C, 181S, 190Q and 236L and resistance towards delavirdine, 101H, 101P, 103H, 103S, 103T, 106M, 181S, 190Q and 236L and resistance towards efavirenz, 184V and 41L and 215Y, wherein the 184V resistance mutation reverses the effect of 41L and 215Y mutations on zidovudine 236L mutation, which increases the sensitivity towards nevirapine ii) a second nucleic acid encoding a HIV protease having at least one mutation selected from: 54L, 54M, 54V, 84A, 84C and 84L and resistance towards a protease inhibitors selected from amprenavir, saquinavir, nelfinavir, ritonavir, indinavir.

(c) using the presence of said at least one nucleic acid to evaluate the effectiveness of said antiviral therapy.

The present invention further concerns a method of identifying a drug effective against drug resistant strains of HIV, comprising:

i) providing at least one strain of HIV comprising:

a) at least one HIV reverse transcriptase containing at least one mutation chosen from:

44D, 77L, 115F, 118I, 184V, 208Y, 210W, 211K, 214F, 215F, 215Y, 219E, 219N, and 219Q, and resistance to d4T, 184I and resistance towards lamivudine, 115F and 184V and resistance towards abacavir.

62V, 75T, 77L, 116Y and 151M and resistance towards all nucleoside analogues 101H, 101P, 103H, 103S, 103T, 106M, 181S, and 190Q and resistance towards nevirapine, 101H, 101P, 103H, 103N, 103S, 103T, 106M, 181C, 181S, 190Q and 236L and resistance towards delavirdine, 101H, 101P, 103H, 103S, 103T, 106M, 181S, 190Q and 236L and resistance towards efavirenz, 184V and 41L and 215Y, wherein the 184V resistance mutation reverses the effect of 41L and 215Y mutations on zidovudine 236L mutation, which increases the sensitivity towards nevirapine b) at least one strain of HIV comprising HIV protease containing at least one mutation chosen from: 54L, 54M, 54V, 84A, 84C and 84L and resistance towards a protease inhibitors selected from amprenavir, saquinavir, nelfinavir, ritonavir, indinavir.

ii) determining a phenotypic response of said drug to said strain of HIV; and iii) using said phenotypic response to determine the effectiveness of said drug.

The instant invention provides methods to identify drug effective for treating HIV infected individuals. The present invention further provides for phenotyping methods for assessing HIV therapy of an individual.

The instant invention further provides a method of designing a therapy for treating a patient infected with HIV comprising:

i) collecting a sample from an HIV-infected patient;

ii) determining whether the sample comprises a) at least one nucleic acid encoding HIV reverse transcriptase having at least one mutation chosen from:

44D, 77L, 115F, 118I, 184V, 208Y, 210W, 211K, 214F, 215F, 215Y, 219E, 219N, and 219Q, and resistance to d4T, 184I and resistance towards lamivudine, 115F and 184V and resistance towards abacavir.

62V, 75T, 77L, 116Y and 151M and resistance towards all nucleoside analogues 101H, 101P, 103H, 103S, 103T, 106M, 181S, and 190Q and resistance towards nevirapine, 101H, 101P, 103H, 103N, 103S, 103T, 106M, 181C, 181S, 190Q and 236L and resistance towards delavirdine, 101H, 101P, 103H, 103S, 103T, 106M, 181S, 190Q and 236L and resistance towards efavirenz, 184V and 41L and 215Y, wherein the 184V resistance mutation reverses the effect of 41L and 215Y mutations on zidovudine 236L mutation, which increases the sensitivity towards nevirapine b) at least one nucleic acid encoding HIV protease having at least one mutation chosen from 54L, 54M, 54V, 84A, 84C and 84L and resistance towards a protease inhibitors selected from amprenavir, saquinavir, nelfinavir, ritonavir, indinavir.

iii) using the presence of said at least one nucleic acid to design the therapy for said patient.

Preferentially at least an additional mutation is present in the HIV protease nucleic acid selected from 10I, 20R, 20T, 24I, 33F, 33I, 33L, 36I, 46L, 71T, 71V, 77I, 77V, 82I, 82V or 90M. More preferential, HIV protease nucleic acid having a mutation at codon 54 comprises at least an additional mutation selected from codon 10 and 90 and confers resistance to a protease inhibitor selected from Amprenavir, Indinavir, Nelfinavir, Ritonavir and Saquinavir. In one embodiment the instant invention provides for a chimaeric HIV virus comprising at least one mutation of the instant invention Not to be limited as to theory, the invention may utilize a combinational approach involving genotypic and phenotypic resistance testing to correlate mutations with resistance phenotypes. Without the specific combination of the technologies mentioned above, this correlation between mutation and resistance would not have been detected. In addition to the observation of these genotypic and phenotypic profiles in isolates from routine clinical practice, site-directed mutants were generated to confirm that these mutations actually form the basis of this pattern of drug resistance.

Resistance of HIV to antiretroviral drugs may be determined at the genotypic level by identifying mutations in the HIV-1 genome and by inferring the resistance of HIV-1 to antiretroviral drugs through searching for mutational patterns known to correlate with resistance. Alternatively, resistance of HIV to antiretroviral drugs may be determined at the phenotypic level by culturing the virus in the presence of the inhibitors, and by measuring to what extent the drug inhibits viral replication. In this case, one measures the effect of all mutational interactions, the effects of genetic changes as yet unknown or not previously identified, the effect of the background genotype, etc., on the phenotype. Assays for detection of mutations in HIV-1 may be based on polymerase chain reaction (PCR) amplification of viral genomic sequences. These amplified sequences are then analyzed using either hybridization or sequencing techniques. Hybridization-based assays include primer-specific PCR, which makes use of synthetic oligonucleotides designed to allow selective priming of DNA synthesis. See Larder, B. A., et al., *AIDS* 5, 137-144 (1991); Richman, D. D., et al., *J. Infect. Dis.* 164, 1075-1081 (1991); Gingeras, T. R., et al., *J. Infect. Dis.* 164, 1066-1074 (1991). Only when primer sequences match the target sequence (wild-type or mutant) at the 3' end, is amplification of target sequences possible and DNA fragments are produced. Knowledge of the primer sequences allows one to infer the sequence of the viral isolate under investigation, but only for the region covered by the primer sequences. Other hybridization-based assays include differential hybridization (Eastman, P. S., et al., *J. Acg. Imm. Def. Syndr. Human Retrovirol.* 9, 264-273 (1995); Holodniy, M., et al., *J. Virol.* 69, 3510-3516 (1995); Eastman, P. S., et al., *J. Clin. Micro.* 33, 2777-2780 (1995).); Line Probe Assay (LiPAJ HIV-11 RT, Innogenetics) (Stuyver, L., et al., *Antimicrob. Agents Chemotherap.* 41, 284-291 (1997).); and GENECHIP® technology (Affymetrix) (D'Aquila, R. T. *Clin. Diagnost*. Virol. 3, 299-316 (1995); Fodor, S. P. A. et al., Nature 364, 555-556 (1993); Fodor, S. P. A. *Nature* 227, 393-395 (1997). DNA sequencing assays, on the other hand, provides information on all nucleotides of the sequenced region. Target sequences are amplified by PCR. Sequencing results may be reported as amino acid changes at positions in the protease gene and the reverse transcriptase gene compared to the wild-type reference sequence. The changes included in the genotyping report may be limited to mutations at positions known to manifest drug resistance-associated polymorphisms. Polymorphisms at positions not associated with drug resistance are not required.

Phenotyping assays measure the ability of a replicating virus to grow in the presence of specific inhibitors compared to a wild-type sensitive reference virus. Consequently, these assays directly measure the degree of viral resistance or susceptibility to specific inhibitors. Applicable phenotyping assays include but are not limited to: the PBMC (peripheral blood mononuclear cells) p24 Antigen Assay, which was the first standardized assay for determination of viral drug resistance in clinical HIV-1 isolates (Japour, A. J., et al., *Antimicrob. Agents Chemother.* 37, 1095-1101 (1993); Kusumi, K. et al., *J. Virol.* 66, 875-885 (1992); and the Recombinant Virus Assays (RVAs) which was first described as an alternative means of assessing phenotypic resistance to RT-inhibitors (Kellam, P. & Larder, B. A., *Antimicrob. Agents Chemother.* 38, 23-30 (1994); and Pauwels, R., et al., *2nd International Workshop on HIV Drug Resistance and Treatment Strategies*, Lake Maggiore, Italy. Abstr. 51 (1998).

As is the case with the genotyping assays, the recombinant virus assay starts with the amplification of viral target sequences by means of PCR. The amplicons are incorporated into a proviral laboratory clone with sequences homologous to those present in the amplicon deleted. This generates a stock of chimeric viruses. The viruses are tested for their ability to grow in the presence of different concentrations of drugs. Results are obtained by calculating $IC_{50}$ values for each inhibitor and by reporting the results as $IC_{50}$ values, expressed in μM concentrations, or by computing the ratio of the $IC_{50}$ values found for the chimeric virus to the $IC_{50}$ values found for a wild type susceptible laboratory virus tested in parallel. In the latter case, resistance is expressed as "fold-resistance" compared to a wild-type susceptible HIV-1 strain. In order to meet the need for high-volume testing and a short turn-around time for an individual test, the latest generation of phenotyping assays has undergone further modifications. The use of reporter gene systems for susceptibility testing allows the implementation of laboratory automation and standardization. See Pauwels, et al., *J. Virol. Methods* 20, 309-321 (1998); Paulous, S., et al., *International Workshop on HIV Drug Resistance, Treatment Strategies and Eradication*, St. Petersburg, Fla., USA. Abstr. 46 (1997); and Deeks, S. G., et al., *2nd International Workshop on HIV Drug Resistance and Treatment Strategies, Lake Maggiore, Italy. Abstr.* 53 (1998).

The ANTIVIROGRAM® assay (Virco) (WO 97/27480) is based on homologous recombination of patient derived HIV-1 gag/PR/RT sequences into a proviral HIV-1 clone correspondingly deleted for the gag/PR/RT sequences. See Pauwels, et al., *J. Virol. Methods* 20, 309-321 (1998). A similar assay (Phenosense ViroLogic) is based on enzymatic ligation of patient-derived PR/RT sequences into a correspondingly deleted proviral vector carrying an indicator gene, luciferase, inserted in the deleted HIV-1 envelope gene. See Deeks, S. G., et al., *2nd International Workshop on HIV Drug Resistance and Treatment Strategies*, Lake Maggiore, Italy. Abstr. 53 (1998). Hertogs et al. *Antimicrob. Agents Chemother.* 44(3) 568-573 (2000) the disclosures of which are herein incorporated by reference.

To summarize, the development of high-throughput phenotyping and genotyping assays has allowed the establishment of a database containing the phenotypic resistance data and the genotypic sequences of over 30,000 clinical isolates. Correlative data analysis and mutational cluster analysis of the database enables a search for mutational patterns with accompanying resistance. An example of which is virtual phenotyping (see PCT/EP01/04445 subsequently published as WO/2001/079540).

In one embodiment, a neural network to accurately predict the development of therapeutic agent resistance or sensitivity based upon genotypic and phenotypic information and to accurately define the genetic basis of therapeutic agent resistance can be used. (see U.S. patent application Ser. No. 09/589,167 filed Jun. 8, 2000, issued Jun. 6, 2006 as U.S. Pat. No. 7,058,616, PCT/EP01/06360, subsequently published as WO/2001/095230, the disclosure of which is expressly incorporated herein by reference in its entirety).

Table 1 below lists some of the most commonly occurring resistance-correlated mutations appearing in clinical isolates after treatment with antiretroviral drugs.

TABLE 1

Examples of commonly occurring resistance-correlated mutations appearing in clinical isolates after treatment with antiretroviral drugs.

Protease Inhibitors

| | | |
|---|---|---|
| Primary Mutations: | D30N | Nelfinavir |
| | M46L, V82A | Indinavir |
| | G48V, L90M | Saquinavir |
| | V82A | Ritonavir |
| | I50V | Amprenavir |
| Secondary Mutations: | L101/F/R/V, K20R/M, L24I, V32I, L33F, M36I, M46I, I47V, I54V/L, L63P, A71V/T, G73S, V77I, V82A/F/T/S, I84V, N88D, L90M | |
| Compensatory Mutations | In a PI-resistant mutational background, mutations at gag cleavage site(s) may partially restore viral replicative Efficiency | |

Reverse Transcriptase Inhibitors

| | |
|---|---|
| NRTI Mutations: | M41L, K65R, D67N, T69D, K70R, L74V, V75T/M, M184V, L210W, T215Y/F, K219Q/E |
| MDR Mutations: | A62V, V75I, F77L, F116Y, Q151 M T69S with associated insertions of 1 to 3 amino acids between codons 68 and 70 of RT |
| NNRTI Mutations: | A98G, L100I, K101E, K103N/T, V106A, V108I, V179D/E, Y181 C/l, Y188C/L/H, G190A, P225H, P236L |
| Reversal Mutations: | M184I/V decreases the effect of zidovudine resistance mutations M41 L and T215Y. L74V decreases the effect of zidovudine resistance mutation T215Y. K65R in mutational background (D67N, K70R, T215Y and K219Q) decreases zidovudine resistance. Y181C decreases the effect of zidovudine resistance mutation T215Y. |

The invention contemplates resistance-correlated mutations to any type of HIV treatment therapy including but not limited to mutations conferring resistance to Protease Inhibitors and Reverse Transcriptase Inhibitors (NRTIs, NtRTIs, and NNRTIs) in addition to Multi-Drug Resistant Mutations.

In one embodiment, the invention contemplates mutations conferring resistance to Protease Inhibitors (PIs). Table 1 lists two categories of mutations for all PIs: primary and secondary mutations. Primary mutations may be the major contributor to the development of resistance to a particular drug. Secondary mutations appear either later during the course of therapy and also lead to resistance, or are already present as natural polymorphisms in a PI-naive viral isolate. A great number of secondary mutations enhance resistance to several PI-inhibitors simultaneously. This may lead to broad cross-resistance to this class of inhibitors, although subtle different phenotypic effects of those secondary mutations may exist.

Not to be limited as to theory, mutations occurring in the protease gene may impair cleaving efficiency of the polyprotein by the protease. Compensatory mutations have been found at the gag cleavage sites that allow more efficient cleaving of the sites by proteases that have mutated. Several studies of clinical isolates from protease-treated patients who have acquired PI resistance-correlated mutations have shown mutations at gag p7/p1 and/or p1/p6 sites significantly raised the replicative efficiency of the mutant viruses.

Other mutations within the practice of the invention may confer resistance to NRTIs and NNRTIs. For example, the mutations typically conferring resistance to the NRTI zidovudine are M41L, D67N, K70R, L210W, T215Y and K219Q.

Multiple mutations in HIV-1 reverse transcriptase also may confer high-level resistance to zidovudine and other NRTIs. Multiple mutations, when present, may act synergistically, and susceptibility decreases as the number of resistance-correlated mutations increases. For example, mutations correlated with resistance to didanosine are L74V, K65R. Resistance to lamivudine is also correlated with the emergence of mutations M184V and M184I that confer very high resistance levels in addition to low-level resistance to didanosine, and zalcitabine. A low-level resistance to lamivudine may also be present in the absence of the 184 mutation while resistance to abacavir is correlated with mutations K65R, L74V, Y115F and M184V.

Another embodiment of the invention relates to multi-drug resistance mutations (MDR) and particularly MDRs to NRTIs. For example, the RT mutational constellation A62V, V75T, F77L, F116Y and Q151M together causes resistance to all nucleoside analogues.

Mutations conferring resistance to Non-Nucleoside Reverse Transcriptase inhibitor (NNRTIs) are also contemplated by the invention. For example, resistance-correlated mutations for nevirapine are A98G, L100I, K103N, V106A, V108I, Y181C/I, Y188C and G190A. These mutations are K103/N/T, Y181C and P236L for delavirdine and for resistance to efavirenz, the mutations are L100I, K101E, K103N, V108I, V179D. Y181C and Y188L.

Another aspect of the invention concerns reversal mutations. For example, the M184V lamivudine resistance mutation decreases the effect of zidovudine resistance mutations M41L and T215Y, while the L74V didanosine resistance mutation decreases the effect of zidovudine resistance mutation T215Y. Whether the described reversal effects are phenotypically significant or not, however, may depend on the combinations of mutations that are present.

In another embodiment, mutations may increase sensitivity to inhibitors. For example, the delavirdine mutation, P236L increases sensitivity of this mutant to inhibition by nevirapine and the lamivudine-resistance mutation M184V causes increased susceptibility to adefovir and to PMPA above the non-mutant sequence. This increased sensitivity seems to be reflected in an enhanced treatment outcome.

Novel mutations of HIV-1 reverse transcriptase (Table 2) within the practice of the invention, and their correlated phenotypic drug resistance, include but are not limited to those shown in Table 2.

TABLE 2

Novel RT Mutations and the Correlated Drug Resistance

| Reverse Transcriptase Mutation | Resistant to: |
|---|---|
| 41L | d4T |
| 44D | d4T |
| 62V | d4T |
| 67N | d4T |
| 69D | d4T |
| 69N | d4T |
| 69SXX | d4T |
| 70R | d4T |
| 75A | d4T |
| 75I | d4T |
| 75M | d4T |
| 75T | d4T |
| 77L | d4T |
| 115F | d4T |
| 116Y | d4T |
| 118I | d4T |

TABLE 2-continued

Novel RT Mutations and the Correlated Drug Resistance

| Reverse Transcriptase Mutation | Resistant to: |
|---|---|
| 151M | d4T |
| 184V | d4T |
| 208Y | d4T |
| 210W | d4T |
| 211K | d4T |
| 214F | d4T |
| 215F | d4T |
| 219E | d4T |
| 219N | d4T |
| 219Q | d4T |
| 215Y | d4T |

The existence of a single mutation or any combination of the mutations in Table 2 may confer resistance to d4T or one or more other treatments from the correlated class. Furthermore, if tools are used, such as those described herein, one may take the identified mutation and the correlated-resistance to a class of treatment. Therefore, the invention also provides that the listed mutations and new combination of mutations, armed with the correlated class of drug, can be used to predict new resistance phenotypes such as resistance to additional PIs, NRTIs, NNRTIs, or MDR resistance. Additionally, the existence of a combination of mutations may confer the same or a different drug resistance profile.

The present invention is also drawn to methods of using the correlations of the invention. In one embodiment, the invention provides for a database comprising the correlation between: the presence of at least one mutation in HIV reverse transcriptase and the resistance of at least one strain of HIV to a reverse transcriptase inhibitor (RTI); or the presence of at least one mutation in HIV protease and the resistance of at least one strain of HIV to a protease inhibitor (PI).

In a further embodiment, the database may assist a physician in developing a treatment program or in determining the appropriate HIV therapy or combination therapy. For example, the VIRTUALPHENOTYPE® assay system (Virco) is a diagnostic tool for monitoring HIV-1 drug resistance. The system can be used for studying resistance development in clinical trials of anti-HIV-1 drugs, for improved clinical management of HIV-1 infected patients and for studying epidemiological aspects of drug resistance. It allows for a rapid determination of the drug sensitivity of the HIV-1 population circulating in the plasma of patients who have been exposed to antiretroviral drugs or who have been infected with drug resistant HIV-1 strains.

The invention also provides for a method of monitoring HIV-1 drug resistance using a method such as the one used in the VIRTUALPHENOTYPE®, which combines in one test the determination of the genetic sequence of patient-derived HIV-1 genetic material and the interpretation of sequence variations found in the patient HIV strain with respect to the possible existence of antiviral drug resistance. In one embodiment, mutations associated with resistance to the different nucleoside reverse transcriptase inhibitors zidovudine, (AZT), didanosine (ddI), zalcitabine (ddC), stavudine (d4T), lamivudine (3TC) and abacavir, the nucleotide reverse transcriptase inhibitor adefovir (PMEA), the non-nucleoside reverse transcriptase inhibitors nevirapine, delavirdine and efavirenz, and the protease inhibitors saquinavir, ritonavir, indinavir and nelfinavir, are evaluated.

The methods of monitoring HIV-1 drug resistance, may also be used in combination with phenotypic drug resistance testing of viral isolates. For example, in one embodiment, a phenotypic test is utilized that is based upon the construction of chimeric HIV-1 strains composed of the protease (PR) and reverse transcriptase (RT) gene sequences which are isolated and amplified from the patient viral RNA. These strains may subsequently be recombined inside CD4+ T cells with a standard laboratory isogenic (HXB2) HIV-1 DNA construct from which the PR/RT gene sequences were deleted. The recombinant strains may then be grown in the presence of the above-mentioned antiviral drugs and the susceptibility of the viral isolates may be expressed as fold-change value of the IC50 of the drug on the patient isolates over the IC50 of the drug on a wild-type laboratory reference strain.

In one embodiment, the sample to be tested is prepared from a patient and the genotypic assay is performed through automated population-based full-sequence analysis (ABI). Therefore, the sequencing method used may provide information on all nucleotides of the sequenced region. Sequencing results may be reported as amino acid changes at positions in the protease gene and the reverse transcriptase gene compared to the wild-type reference sequence. The changes included in the genotyping report may be limited to mutations at positions known to manifest drug resistance-associated polymorphisms. Polymorphisms at positions not associated with drug resistance are not required.

In an even further embodiment, a report may be generated that shows the region of the patient virus that has been sequenced, the mutations detected by the test, and/or an interpretation of the evidence obtained. The interpretation may include the antiretroviral drugs, the drug(s) for which a known resistance-associated mutation has been identified and/or to what extent the observed mutations are indicative of resistance to the drugs.

Knowledge of correlated geno- and phenotypes, together with knowledge of the catalytic site on the viral target for new compounds may also be utilized to tailor the construction of new molecules and the implementation of new (combination) treatments for HIV.

In another embodiment, the invention is drawn to a method of evaluating the effectiveness of antiretroviral therapy of an HIV-infected patient comprising: collecting a sample from an HIV-infected patient; and determining whether the sample comprises at least one nucleic acid encoding HIV reverse transcriptase having at least one mutation or HIV protease having at least one mutation. The sample may be a plasma sample, blood cells, or other tissue. Further, the invention has the potential to ameliorate HIV genotypic resistance diagnostics and can, in principle, lead to a better therapy and, under certain conditions, even be life saving.

In a further embodiment, the invention provides for a method of identifying or designing drugs effective against NNRTI or NRTI resistant HIV, the method comprising the steps of: providing at least one strain of HIV comprising a nucleic acid encoding HIV reverse transcriptase containing at least one mutation, and determining the phenotypic response of the HIV strain to a drug. In an even further embodiment, the invention provides a method of identifying drugs effective against PI resistant strains of HIV, wherein the strain of HIV comprises HIV protease containing at least one mutation, and determining the phenotypic response of said strain of HIV to said drug. The invention is also useful for interpretation of resistance of HIV isolates. It can also be used in full sequence analysis of HIV. In addition, the invention has applications for hybridization-based HIV analyses or in drug design, development, testing and marketing. In a further embodiment, the invention includes the drugs designed by the methods of the invention.

The invention also provides for a method of designing therapy for treating patients infected with HIV comprising correlating the presence of HIV reverse transcriptase having at least one mutation described above with resistance to at least one NNRTI or at least one NRTI, or correlating the presence of HIV protease having at least one mutation with resistance to at least one PI.

The identification of the comparative mutations of the invention may lead to improved antiretroviral drug treatment programs. As outlined above, there is ample evidence demonstrating that poor virologic response to drug therapy may be correlated with the existence of genotypic and/or phenotypic viral resistance to one, several, or in the worst case, all available antiretroviral drugs. As a consequence, resistance testing using the correlations of the invention may be used as a tool for identifying those drugs that no longer contribute towards decreasing the plasma viral load.

EXAMPLES

Example 1

The Identification of Mutational Patterns in HIV-1 Reverse Transcriptase and the Correlated Phenotypic Resistance Plasma samples were obtained from HIV-1-infected individuals from routine clinical practice in Europe and the US and were shipped to the laboratory on dry ice and stored at −70° C. until analysis. Phenotypic analysis was performed using the recombinant virus assay. See Kellam, P., and B. A. Larder. *Antimicrob. Agents Chemother.* 38:23-30 (1994); Hertogs, K., et al., *Antimicrob. Agents Chemother.* 42:269-276 (1998); Briefly, protease (PR) and reverse transcriptase (RT) coding sequences were amplified from patient-derived viral RNA with HIV-1 specific primers. After homologous recombination of amplicons into a PR-RT deleted proviral clone, the resulting recombinant viruses were harvested, titrated and used for in vitro susceptibility testing to antiretroviral drugs. The results of this analysis were expressed as fold-resistance values, reflecting the fold-increase in mean $IC_{50}$ (μM) of a particular drug when tested with patient-derived recombinant virus isolates, relative to the mean $IC^{50}$ (μM) of the same drug obtained when tested with a reference wild-type virus isolate (IIIB/LAI).

Genotypic analysis was performed by automated population-based full-sequence analysis (ABI). Results of the genotypic analysis are reported as amino acid changes at positions along the reverse transcriptase gene compared to the wild-type (HXB2) reference sequence. Cluster analysis by VIRTUALPHENOTYPE® interpretational system allowed detection of the occurrence of mutational pattern in the database containing the genetic sequences of the clinical isolates and linkage with the corresponding resistance profiles of the same isolates. (See PCT/EP01/04445, which was subsequently published as WO/2001/079540).

For the modeling studies, mutations were generated in the RT gene of HXB2, a wild-type laboratory HIV-1 strain, using the QuikChange[J] Site-Directed Mutagenesis Kit, STRATAGENE[7], Stratagene Cloning systems, La Jolla, Calif., USA.

Analysis of the Clinical Isolates

Table 3 reports the frequency of mutations 44D/A, 118I, 184V, 215Y, and 41L in RT in clinical isolates with various levels of phenotypic resistance to zidovudine (ZDV) and lamivudine (3TC). The mutant isolates described here were drawn from a pool of clinical isolates.

Table 3 reports the frequency of mutations 44D/A, 118L, 184V, 215Y, and 41L in RT in clinical isolates with various levels of phenotypic resistance to zidovudine (ZDV) and lamivudine (3TC). The mutant isolates described here were drawn from a pool of clinical isolates.

TABLE 3

Frequency of ZDV and 3TC Resistance-correlated Mutations in Clinical Isolates Susceptible or Resistant to ZDV and/or 3TC Compared to a Sample of Fully Susceptible Isolates

| | Frequency (%) of mutations | | | | | |
|---|---|---|---|---|---|---|
| | ZDV resistance-correlated mutations | | 3TC resistance-correlated mutations | | | No. of |
| Resistance Class[a] | 41L | 215Y | 184V | 44D/A | 118I | samples |
| ZDV (<4), 3TC (<4) | 4.5 | 4.8 | 0 | 1.3 | 3.1 | 314 |
| ZDV (<4), 3TC (>10) | 18.3 | 18.8 | 90 | 1.3 | 6.3 | 240 |
| ZDV (>10), 3TC (<4) | 59.5 | 68.9 | 0 | 14.9 | 18.9 | 74 |
| ZDV (>10), 3TC (4, <50) | 77 | 72.2 | 4 | 30.2 | 39.7 | 126 |
| ZDV (>10), 3TC (50) | 77.5 | 66.9 | 84.1 | 28.5 | 37.8 | 151 |

[a]Resistance (in parentheses) is expressed as the fold increase in the mean $IC_{50}$ of the drug relative to the mean $IC_{50}$ of the same drug for a wild-type reference laboratory HIV-1 strain.

Isolates that are susceptible (WT) to both ZDV and 3TC (n=195): the frequency of any of the six mutations listed above was low.

Isolates that are resistant to ZDV (>10-fold, n=220): Table 3 shows that the ZDV resistance-correlated mutations 215Y, 41L and 70R were high in frequency in this category and throughout all 3TC resistance categories. Mutation 184V was the predominant mutation in the high-resistance 3TC class (>50-fold), whereas 184V was rare in the intermediate 3TC resistance group and absent in the low-level resistance group and the 3TC susceptible group. The mutations 44D/A and 118I were present in all 3TC resistance categories.

Isolates that are resistant to 3TC (>10-fold, n=295): Table 3 shows that the frequency of the high-level 3TC resistance-correlated mutation, 184V, was high in all ZDV resistance categories (low, intermediate and high) and was the predominant mutation in the ZDV susceptible and intermediate-resistance group. As the resistance to ZDV increased, so did the frequency of the ZDV resistance-correlated mutations 41L, 70R and 215Y, while the frequency of mutation 184V decreased. Mutations 44D/A and 118I also substantially increased in frequency as resistance to ZDV increased.

The results thus far show that low and intermediate resistance to 3TC was not related to the presence of mutation 184V. Indeed, this mutation was practically absent in these classes. Table 3 further indicates that mutations 44D/A and 118I were present in high frequencies only in the presence of ZDV resistance mutations 215Y, 41L and 70R. In the isolates that were susceptible to ZDV, the frequency of ZDV resistance-correlated mutations was low and 44A/D and 118I were also rare, even though 3TC resistance was greater than 10-fold. In this group the high frequency of 184V accounted for the resistance to 3TC.

Analysis of the Mutants Generated by Site-directed Mutagenesis

Table 4 shows the codon changes introduced into a wild-type HXB2 background together with the fold-resistance values obtained when the different mutants were tested in the drug susceptibility assay. All six mutants carrying mutation 184V were highly resistant to 3TC. Two of them carried both 44D/A and 118I, while all but one (SDM23) carried ZDV resistance-correlated mutations.

TABLE 4

3TC and ZDV resistance-correlated mutations and phenotypic resistance in mutants with site-directed mutations

| | | 3TC resistance profile | | AZT resistance profile | | |
|---|---|---|---|---|---|---|
| Mutant | Mutation(s) | Fold resistance[a] | n[b] | Mutations | Fold resistance | |
| SDM05 | | 4 (0.3)[c] | | 41L, 210W, 211K, 214F, 215Y | 64 (15.0) | 5 |
| SDM18 | | 2 (0.6) | | 41L, 67N, 210W, 211K, 214F, 215Y | 45 (13.4) | 3 |
| SDM19 | | 4 (0.7) | | 41L, 67N, 69D, 210W, 211K, 214F, 215Y | 46 (18.2) | 2 |
| SDM28 | 44D | 1 (0.1) | | | 2 (0.3) | 6 |
| SDM31 | 44D | 22 (2.5) | | 41L, 67N, 210W, 211K, 214F, 215Y | 48 (11.8) | 4 |
| SDM32 | 44D | 8 (2.2) | | 41L, 67N, 69D, 210W, 211K, 214F, 215Y | 49 (5.9) | 6 |
| SDM29 | 118I | 2 (0.2) | | | 2 (0.4) | 6 |
| SDM33 | 118I | 7 (1.0) | | 41L, 67N, 210W, 211K, 214F, 215Y | 49 (8.0) | 6 |
| SDM34 | 118I | 32 (3.9) | | 41L, 67N, 69D, 210W, 211K, 214F, 215Y | 34 (14.4) | 5 |
| SDM30 | 44D, 118I | 3 (0.3) | | | 1 (0.4) | 6 |
| SDM35 | 44D, 118I | 14 (1.4) | | 41L, 67N, 210W, 211K, 214F, 215Y | 49 (9.6) | 5 |
| SDM36 | 44D, 118I | 15 (2.1) | | 41L, 67N, 69D, 210W, 211K, 214D, 215Y | 49 (10.6) | 5 |
| SDM22 | 184V | 78 (16.3) | | 41L, 210W, 211K, 214F, 215Y | 7 (0.9) | 5 |
| SDM23 | 184V | 82 (13.6) | | | 2 (0.5) | 6 |
| SDM24 | 184V | 85 (14.2) | | 69S-S-S, 210W, 211K, 214D, 215Y | 27 (16.2) | 5 |
| SDM26 | 184V | 72 (13.8) | | 41L, 67N, 210W, 211K, 214F, 215Y | 25 (1.4) | 5 |
| SDM38 | 184V, 44D, 118I | 82 (13.5) | | 41L, 210W, 211K, 214F, 215Y | 20 (4.1) | 6 |
| SDM39 | 184V, 44D, 118I | 84 (13.9) | | 41L, 67N, 69D, 210W, 211K, 214F, 215Y | 21 (5.3) | 5 |

[a]Fold increase in the mean $IC_{50}$ of the drug relative to the mean $IC_{50}$ of the same drug for a wild-type reference laboratory HIV-1 strain.
[b]n, number of replicate tests run for each phenotype drug resistance determination.
[c]Standard errors are indicated in parentheses.

All of the mutants followed the predicted ZDV resistance or susceptibility pattern. At the same time, three mutants were generated with a change at codon 44, three with a change at codon 118 and three with a change at both codons 44 and 118. Within each of these three groups two mutants also carried changes at positions correlated with resistance to ZDV, whereas one mutant remained wild-type at those codons. The drug resistance values listed in Table 4 clearly show that the presence of mutations at codon 44 and 118, singly or together, can cause intermediate resistance to 3TC (8 to 32-fold), distinguishable from the high resistance to 3TC (>62-fold) caused by mutation 184V. Moreover, the intermediate resistance to 3TC was only observed when mutations at positions 44 and/or 118 occurred in a ZDV-resistant background (41L, 67N, 210W, 215Y) while resistance caused by mutation 184V was obviously not related to ZDV resistance.

Relationship Between the Presence of Changes at RT Positions 44 or 118 in Clinical Samples and Antiretroviral Therapy As can be deduced from Table 4, changes at position 44 and 118 may occur in virus samples with or without the M184V substitution, but they appeared at higher incidence in samples with ZDV resistance. It was therefore of interest to look at the antiretroviral treatments administered to patients with HIV-isolates that contained 44D or 118I. We identified a subset of 86 samples with 44D and 88 samples with 118I originating from patients for whom antiretroviral histories were available. Although it was not possible to draw conclusions regarding the incidence of changes at 44 or 118 from this subset according to treatment history, as this was not a randomized study, this analysis nevertheless shed some light on the conditions that may lead to mutations at these positions.

For the 44D subset, 50/86 of the samples originated from patients who were receiving lamivudine at the sample date and 5 patients in this subset had never received 3TC prior and up to the sample date. All 5 patients had received zidovudine/didanosine at some time and all HIV-isolates were wild-type at position 184. The zidovudine treatment experience was extensive, as expected for historical reasons. All except one patient had received zidovudine in combination with other NRTI's and 70/86 had also received zidovudine monotherapy in the past. The one patient reported to be zidovudine naive had received stavudine. This sample contained 41L and 215Y.

Results for 118I subset were similar in that 55/88 samples originated from patients who were on lamivudine at the sample date and 2 patients had never received lamivudine (both had received zidovudine plus didanosine). Most patients, 83/88, had received zidovudine in combination with other NRTI's, and 70 had also received zidovudine monotherapy. The 5/88 zidovudine naive patients had received stavudine. For a few patients, consecutive samples showing the evolution of 44D or 118I were available.

These results indicate that mutations E44D/A and V118I in HIV-1 RT confer a low to intermediate level of resistance to 3TC when they occur in clinical isolates possessing a ZDV-resistant background. The cluster analysis of genotypically and phenotypically characterized clinical isolates and the results from the site-directed mutagenesis experiment confirm that indeed mutations at codons 44 and 118 are correlated with low and intermediate level of resistance to 3TC, with the restriction that ZDV resistance-correlated mutations be present. Additionally, the analysis of the clinical samples for which therapy histories were available and in which prior ZDV exposure was shown to be extensive, confirmed the results obtained from our large clinical data set in that mutations 44D/A and 118I appeared in the context of ZDV mutations.

Mutations 44D/A and 118I each are capable of independently generating resistance to 3TC. The experiment with site-directed mutagenesis does not indicate the existence of synergistic effects between the two mutants with respect to their phenotypic effect on 3TC resistance.

Example 2

Determining the Genetic Basis of HIV-1 Multi-Nucleoside Resistance

892 HIV-1 samples were surveyed in our resistance database from patients failing therapy using a standardized recombinant-based phenotypic assay and by DNA sequence analysis. Multi-nucleoside resistance was correlated with complex mutational patterns in the RT coding region. Plasma samples were obtained from patients who had received anti-retroviral therapy. Selection was on the basis of a viral load >1000 HIV-1 RNA copies/ml and for the purpose of this study, patients with this level of plasma HIV-1 were considered to be failing therapy.

Viral RNA was extracted from 200 µL patient plasma using the QIAAMPV® Viral RNA Extraction Kit (Qiagen, Hilden, Germany), according to the manufacturers instructions. cDNA encompassing part of the pol gene was produced using EXPAND™ reverse transcriptase (Boehringer Mannheim) as described previously. See Hertogs K., et al., *Antimicrob. Agents Chemother.* 42:269-276 (1998). A 2.2 kb fragment encoding the protease and RT regions was then amplified by nested polymerase chain reaction (PCR) using PCR primers and conditions as described. Id. This genetic material was subsequently used in both phenotyping and genotyping experiments.

MT-4 cells (Harada S., et al, *Science* 229:563-566(1985).) were co-transfected with pol gene PCR fragments and the protease-RT deleted HIV-1 molecular clone, pGEM3deltaPRT, as described. See Hertogs K., et al., *Antimicrob. Agents Chemother.* 42:269-276 (1998). This resulted in viable recombinant viruses containing protease/RT from the donor PCR fragment. Phenotypic susceptibility to nucleoside analogues was determined using an MT-4 cell viral cytopathic effect (CPE) protection assay as described. Id. Fold resistance values were derived by dividing the mean $IC_{50}$ for a patient's recombinant virus by the mean $IC_{50}$ for wild-type control virus (strain HXB2-D). The PCR products obtained from patient plasma samples were genotyped by dideoxy-nucleotide-based sequence analysis. Samples were sequenced using the BIGDYE™ terminator kit (Applied Biosystems, Inc. (ABI)) and resolved on an ABI 377 DNA sequencer.

Mutations in the RT coding region were created by site-directed mutagenesis of a wild-type HXB2-D EcoRl-Pstl restriction enzyme fragment, encompassing the HIV-1 pol gene and cloned into pGEM3 (Promega). Single and multiple nucleotide changes were introduced into RT using the EXSITE™ mutagenesis kit (Strategene). All mutant clones were verified by DNA sequence analysis of the entire RT. PCR fragments were prepared from the mutated clones and the altered RT coding regions were transferred into the HIV-1 HXB2-D genetic background by homologous recombination as described above. The susceptibility of these recombinant viruses to nucleoside analogues was subsequently determined by the MT-4 cell CPE protection assay. Id.

Phenotypic Susceptibility Analysis

The recombinant virus assay (ANTIVIROGRAM®) was used to determine simultaneously the susceptibility of the samples to AZT, 3TC, d4T ddl and ddC. From this analysis, 302 samples were identified with four-fold or greater increases in $IC_{50}$ (relative to a wild-type control virus) to at least four of these inhibitors. Thus, a substantial number of MDR viruses were present in the sample population.

Genotypic Analysis of Multi-nucleoside Resistant Samples

Figure 2:
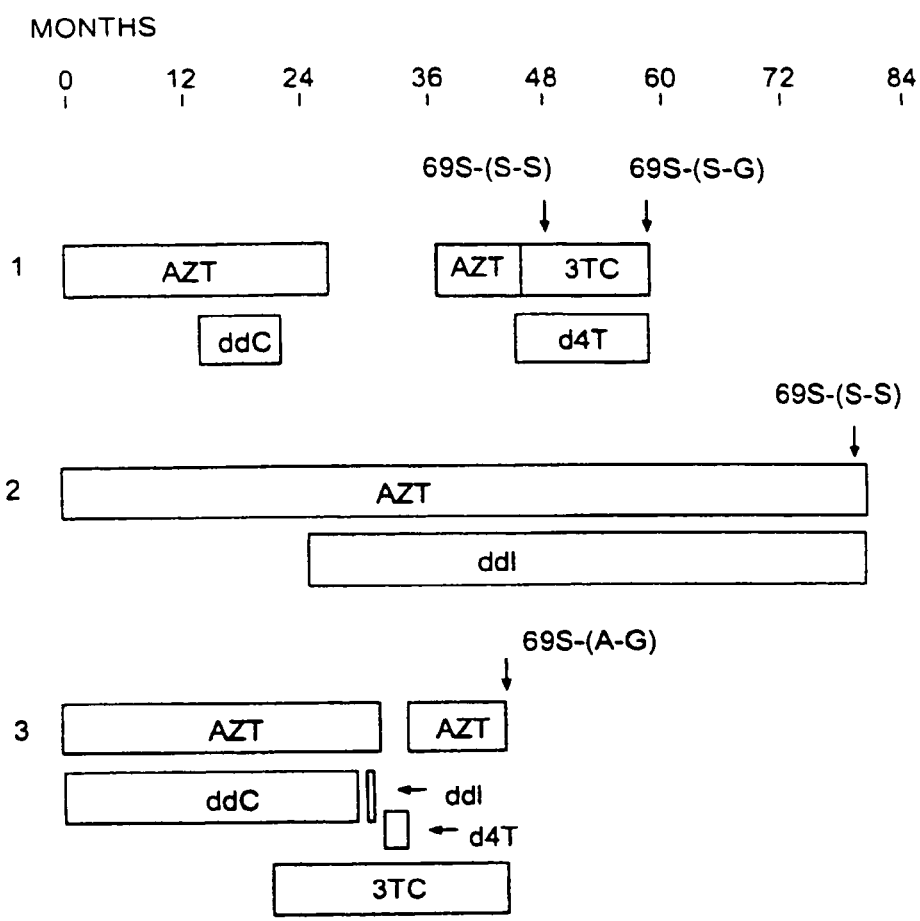
FIG. 2: Therapy histories of three patients whose HIV-1 isolates developed codon 69 insertions. Nucleoside analogue therapies (AZT, 3TC, ddC, ddI or d4T) are shown as horizontal bars, indicating the time period in which each patient (1, 2 or 3) received a particular treatment. The time point at which plasma samples were obtained for genotypic and phenotypic analysis are shown by the arrows together with the specific codon 69 insertion detected. Any other therapies besides nucleosides that these patients may have been receiving are not indicated on this figure.

Genotypic analysis was performed on all 892 samples by dideoxy-nucleotide sequencing. Complex patterns of multiple mutations were seen in the RT coding regions of the MDR samples. These included combinations of AZT and 3TC resistance mutations (particularly 41L, 67N, 210W and 215Y with 184V/I) plus mutations at codons 69 (T69A/N) and/or 75 (V75M). This analysis highlighted the incidence of the codon 151 mutational cluster in the MDR group. In addition, a novel family of amino acid insertions and rearrangements between codons 67 and 70 were also prevalent in the MDR group. These two patterns of mutations were correlated with high-level phenotypic multi-nucleoside resistance (FIG. 2), 27 samples having the codon 151 cluster and 45 samples having insertions and rearrangements (typically a T69S substitution, followed by insertion of two amino acids). The mean fold increases in $IC_{50}$ to d4T, ddl and ddC for these different groups are shown in FIG. 2. This analysis indicated that codon 69 insertion mutants had a high degree of d4T and ddC resistance (>10-fold), which was also seen with the codon 151 cluster. However, samples with AZT and 3TC resistance mutations plus T69A/N or V175M showed only modest levels of resistance to these drugs (FIG. 2). Not surprisingly, all four groups shown in FIG. 2 were highly resistant to AZT and 3TC (mean fold increase in AZT $IC_{50}$ of >500-fold and >30-fold for 3TC). This was because many MDR samples contained mutations conferring AZT resistance (e.g., 41L, 67N, 210W and 215Y) and 3TC resistance (Met184V/I).

Spectrum of Different Insertions Seen in the RT Codon 67 to 70 Region

The extensive variety of insertions in the, codon 67 to 70 region of RT is summarized in Table 3. The largest group (n=16) had a T69S substitution followed by insertion of two S residues. The next largest group (n=10) also had a T69S substitution but in this case a different insertion of S-G. Samples with a number of different double amino acids inserted after 69Ser were also identified. In addition, insertions of two or three amino acids between codons 68 and 69 were also seen. The positions of these insertions were based on the fact that T69 and L70 were contiguous. In some samples there were rarely observed substitutions at codon 67 (A67G/S/G), rather than the common 67N AZT resistance mutation. In two samples deletion of codon 70 was observed (after insertion of three residues between codons 68 and 69), and a single substitution of T69S without an insertion was seen in four samples (Table 3). The inserted residues did not show any obvious patterns in terms of codon usage. For example, the S-S insertions were rarely direct repeats of the S69 codon, suggesting that simple reiterations of S69 could not account for the appearance of these insertions in the RT.

Patients' Therapy Patterns in Relation to Codon 69 Insertions

The codon 69 insertions were always present in a background of AZT resistance mutations, especially T215Y/F. This may not be surprising as therapy histories from many of the patients whose samples were analyzed in this study revealed a common pattern of AZT therapy, followed by combination therapy with nucleosides and protease inhibitors (data not shown). FIG. 3 shows typical treatment patterns for three patients, indicating the time samples were obtained for virological analysis. It was not possible from these histories to determine precisely the nucleoside analog(s) responsible for selecting codon 69 insertions. Sequential samples from patient 1 revealed an interesting transition of 69S-[S-S] to 69S-[S-G] during a period of 3TC/d4T combination therapy.

Susceptibility Analysis of HIV-1 Variants Constructed by Site-directed Mutagenesis To investigate the significance of the observed mutational patterns correlated with MDR virus we constructed a series of viruses by site-directed mutagenesis with specific changes in a defined genetic background (HXB2-D). T69A or V75M in a background of AZT mutations conferred little or no resistance to 3TC, d4T, ddl or ddC. Variants were also constructed with 69S-[S-S], either alone or together with two AZT resistance mutations (210W and 215Y). In addition, the potential role of A62V, a substitution also frequently correlated with the insertions was investigated by adding this mutation to a background of 69S-[S-S] plus 210W/215Y. Susceptibility data for six nucleoside analogues are summarized in Table 4. These data showed that the 69S-[S-S] insertion alone did not confer multi-nucleoside resistance. In fact, this virus only had a significant decrease in susceptibility to 3TC. By contrast, the variants with the insert plus AZT resistance mutations had decreased susceptibility to AZT, 3TC, d4T, ddC and abacavir (4-[(2-amino-6-cyclopropyl-amino)-9H-purin-9-yl]-2-cyclopentene-1-methanol, 1592U89), confirming that the 69 insertions plus AZT mutations conferred the MDR phenotype.

Example 3

Use of Neural Networks to Define the Genetic Basis of HIV-1 Resistance to d4T

Three neural network models (the 9RT, 26RT and 60RT models) were developed to investigate how mutation patterns influence d4T resistance. The 9 RT model was based on the nine mutations listed in the Stanford University HIV Drug Resistance Database (hivdb.stanford.edu) associated with d4T resistance (62V, 69D, 69N, 69SXX, 75I, 75T, 77L, 116Y, and 151M). The other models were based on adding either the next 17 or 51 most frequent RT mutations present in d4T resistant samples. Thus, the 26 RT mutation model included the 9 RT mutation model plus the 17 most frequent mutations in d4T resistant samples. These 17 mutations were 41L, 44D, 67N, 70R, 75A, 75M, 115F, 181I, 184V, 208Y, 210W, 214F, 215F, 215Y, 219E, 219N, and 219Q. The 60 RT mutation model consisted of the 26 RT mutation model, plus the 34 next most frequent mutations in d4T resistant samples. These 34 mutations were 20R, 35I, 39A, 43E, 60I, 65R, 122K, 123E, 135T, 162C, 177E, 196E, 200A, 207E, 211K, 228H, 272A, 277K, 286A, 293V, 297K, 329L, 356K, 357T, 358K, 359S, 360T, 371V, 375V, 376A, 386I, 390R, 399D, and 400A. In order to discover which mutations had contributed to this improved prediction, improved sample IS9-26 and IS9-60 were identified by comparing the phenotypic outputs of the 9-model and 26-model, and the 9-model and 60-model on the test set. The corresponding genotypes of the improved samples were collected and analyzed, all extra mutations contained in the improved samples were screened out, and the frequency of each mutation found in IS9-26 and IS9-60 was calculated and compared with that of the mutation being found in the whole samples. All mutations with higher difference of two frequencies were identified and considered to play a role in conferring resistance to d4T. In this example, the threshold frequency was set to 9%. The following mutations were identified from the 9- and 26-models: 41L (44%-79%), 44D (13%-26%), 67N (36%-56%), 70R (21%-30%), 118I (21%-36%), 210W (34%-65%), and 215Y (44%-81%). The following mutations were identified from the 9- and 60-models: 41L (44%-73%), 67N (36%-56%), 181I (21%-32%), 210W (34%-62%), 211K (49%-59%), and 215Y (44%-74%). In conclusion, these results show that at least 17 RT mutations (the 8 identified here plus the 9 identified above from the Stanford Database) may confer d4T resistance, including AZT resistance mutations. The results also identified 10 other mutations that may also confer resistance: 184V(36%-42%), 214F(88%-94%), 75A(0.7%-0.6%), 75M(4%-8%), 115F (1%-0.2%), 208Y(13%-21%), 215F(9%-111%), 219E(5%-4%), 219N(4%-11%), and 219Q(12%-16%).

Example 4

Overview of the mean fold increase in resistance and the effect of the 101 mutations in the HIV reverse transcriptase gene sequence. The fold increase in resistance is calculated from the increase in the mean $IC_{50}$ of the drug relative to the mean $IC_{50}$ of the same drug for a wild-type reference laboratory HIV-1 strain. The effect of the mutations was investigated on Nevirapine, Delavirdine and Efavirenz. The results are displayed as mean fold increase and the standard deviation thereof.

TABLE 5

Overview of the reverse transcriptase mutations at position 101 and their corresponding influence on the resistance towards reverse transcriptase inhibitors. The data are expressed as fold increase in resistance compared to a laboratory reference strain (WT).

| Genotype | Nevirapine | Delavirdine | Efavirenz |
|---|---|---|---|
| WT | 1.3 | 1.8 | 0.9 |
| n | 20 | 19 | 20 |
| Stdev | 0.5 | 0.6 | 0.8 |
| 101E | 4.9 | 7.7 | 2.4 |
| n | 5 | 5 | 5 |
| Stdev | 5.8 | 20.4 | 2.7 |
| 101Q | 1.9 | 1.2 | 0.9 |
| n | 5 | 5 | 5 |
| Stdev | 2.4 | 1.5 | 1.0 |
| 101P | 53.4 | 162.4 | 84.2 |
| n | 20 | 17 | 18 |
| Stdev | 14.3 | 77.8 | 81.4 |
| 101H | 24.0 | 45.5 | 3.5 |
| n | 23 | 23 | 23 |
| Stdev | 14.8 | 65.4 | 3.1 |

Example 5

Overview of the mean fold increase in resistance and the effect of the 103 mutations in the HIV reverse transcriptase gene sequence. The fold increase in resistance is calculated from the increase in the mean $IC_{50}$ of the drug relative to the mean $IC_{50}$ of the same drug for a wild-type reference laboratory HIV-1 strain. The results are displayed as mean fold increase and the standard deviation thereof.

TABLE 6

Overview of the reverse transcriptase mutation at position 103 and their corresponding influence on the resistance towards reverse transcriptase inhibitors. The data are expressed as mean fold increase in resistance compared to a laboratory reference strain (WT).

| Genotype | Nevirapine | Delavirdine | Efavirenz |
|---|---|---|---|
| WT | 1.3 | 1.8 | 0.9 |
| n | 20 | 19 | 20 |
| Stdev | 0.5 | 0.6 | 0.8 |
| 103N | 48.1 | 176.1 | 486.8 |
| n | 10 | 10 | 10 |
| Stdev | 13.8 | 83.8 | 153.3 |
| 103R | 1.1 | 1.6 | 0.6 |
| n | 5 | 5 | 5 |
| Stdev | 2.8 | 2.1 | 1.3 |
| 103T | 43.7 | 84.5 | 2.8 |
| n | 4 | 4 | 4 |
| Stdev | 32.0 | 61.7 | 1.2 |
| 103H | 69.4 | 191.6 | 52.7 |
| n | 5 | 5 | 5 |
| Stdev | 16.5 | 105.2 | 23.4 |
| 103S | 45.4 | 18.3 | 8.4 |
| n | 19 | 15 | 18 |
| Stdev | 9.0 | 9.6 | 3.8 |

Example 6

Overview of the mean fold increase in resistance and the effect of the 181 mutations in the HIV reverse transcriptase gene sequence. The fold increase in resistance is calculated from the increase in the mean $IC_{50}$ of the drug relative to the mean $IC_{50}$ of the same drug for a wild-type reference laboratory HIV-1 strain. The results are displayed as mean fold increase and the standard deviation thereof.

TABLE 7

Overview of the reverse transcriptase mutation at position 181 and their corresponding influence on the resistance towards reversetranscriptase inhibitors. The data are expressed as fold increase in resistance compared to a laboratory reference strain (WT).

| Genotype | Nevirapine | Delavirdine | Efavirenz |
|---|---|---|---|
| WT | 1.3 | 1.8 | 0.9 |
| n | 20 | 19 | 20 |
| Stdev | 0.5 | 0.6 | 0.8 |
| 181C | 56.0 | 82.5 | 2.0 |
| n | 11 | 11 | 11 |
| Stdev | 8.4 | 59.2 | 0.8 |
| 181I | 63.8 | 81.7 | 2.0 |
| n | 5 | 5 | 5 |
| Stdev | 20.1 | 57.9 | 1.0 |
| 181S | 82.8 | 147.9 | 8.7 |
| n | 5 | 5 | 4 |
| Stdev | 21.7 | 64.4 | 3.5 |

Example 7

Overview of the mean fold increase in resistance and the effect of the 190 mutations in the HIV reverse transcriptase gene sequence. The fold increase in resistance is calculated from the increase in the mean $IC_{50}$ of the drug relative to the mean $IC_{50}$ of the same drug for a wild-type reference laboratory HIV-1 strain. The results are displayed as mean fold increase and the standard deviation thereof.

TABLE 8

Overview of the reverse transcriptase mutation at position 190 and their corresponding influence on the resistance towards reverse transcriptase inhibitors. The data are expressed as fold increase in resistance compared to a laboratory reference strain (WT).

| Genotype | Nevirapine | Delavirdine | Efavirenz |
|---|---|---|---|
| WT | 1.3 | 1.8 | 0.9 |
| n | 20 | 19 | 20 |
| Stdev | 0.5 | 0.6 | 0.8 |
| 190A | 60.7 | 2.3 | 24.8 |
| n | 4 | 4 | 4 |
| Stdev | 12.6 | 0.7 | 11.3 |
| 190S | 75.9 | 1.9 | 483.6 |
| n | 6 | 6 | 6 |
| Stdev | 21.8 | 3.4 | 231.1 |
| 190E | 40.0 | 131.1 | 385.3 |
| n | 24 | 22 | 24 |
| Stdev | 7.3 | 61.2 | 22.0 |
| 190Q | 52.7 | 34.0 | 401.1 |
| n | 22 | 21 | 22 |
| Stdev | 8.8 | 58.9 | 22.5 |

Example 8

Fold Increase in Resistance of Protease Inhibitors by the 84A Mutation (in a Background)

TABLE 9

Overview of the mean fold increase in resistance and the effect of the 84A mutation in the HIV protease sequence. The fold increase in resistance is calculated from the increase in the mean $IC_{50}$ of the drug relative to the mean $IC_{50}$ of the same drug for a wild-type reference laboratory HIV-1 strain.

| # | Genotype | Indinavir | Ritonavir | Nelfinavir | Saquinavir | Amprenavir |
|---|---|---|---|---|---|---|
| 1 | WT | 0.9 | 0.6 | 0.7 | 0.9 | 1 |
|   | n | 6 | 6 | 6 | 6 | 6 |
|   | Stdev | 0.5 | 0.4 | 0.2 | 0.2 | 0.4 |
| 2 | 10I | 0.7 | 1.15 | 1 | 0.9 | 1.1 |
|   | n | 4 | 4 | 4 | 4 | 4 |
|   | Stdev | 0.2 | 0.7 | 0.6 | 0.3 | 0.4 |
| 3 | 46I | 0.6 | 0.8 | 1.5 | 0.6 | 1.2 |
|   | n | 5 | 5 | 5 | 5 | 5 |
|   | Stdev | 0.6 | 0.8 | 0.9 | 0.2 | 0.2 |
| 4 | 46I + 84V | 2.6 | 4.6 | 5.6 | 2.5 | 2.3 |
|   | n | 2 | 2 | 2 | 2 | 2 |
|   | Stdev | 2.1 | 1.6 | 4.5 | 2.4 | 3.0 |
| 5 | 46I + 84A | 26.8 | 51.8 | 61.9 | 38.1 | 7.7 |
|   | n | 5 | 5 | 5 | 5 | 5 |
|   | Stdev | 20.9 | 39.1 | 18.1 | 11 | 25.3 |
| 6 | 10I + 46I | 2.9 | 1.5 | 0.8 | 0.5 | 5.6 |
|   | n | 5 | 5 | 5 | 5 | 5 |
|   | Stdev | 3.7 | 0.3 | 0.7 | 0.3 | 2.9 |
| 7 | 10I + 46I + 84V | 2.4 | 11.9 | 3.1 | 4.1 | 4.5 |
|   | n | 4 | 4 | 4 | 4 | 4 |
|   | Stdev | 1.5 | 7.1 | 3.1 | 2.7 | 4.1 |
| 8 | 10I + 46I + 84A | 33.4 | 77.3 | 43.9 | 48.2 | 17 |
|   | n | 5 | 5 | 5 | 5 | 5 |
|   | Stdev | 29.9 | 38.3 | 25 | 9.6 | 31.1 |
| 9 | 10L/I + 46I + 84A | 44.5 | 114 | 56.2 | 46.4 | 24.9 |
|   | n | 5 | 5 | 5 | 5 | 5 |
|   | Stdev | 22.9 | 44.4 | 12.5 | 9.5 | 8.2 |

TABLE 9-continued

Overview of the mean fold increase in resistance and the effect of the 84A mutation in the HIV protease sequence. The fold increase in resistance is calculated from the increase in the mean IC$_{50}$ of the drug relative to the mean IC$_{50}$ of the same drug for a wild-type reference laboratory HIV-1 strain.

| # | Genotype | Indinavir | Ritonavir | Nelfinavir | Saquinavir | Amprenavir |
|---|---|---|---|---|---|---|
| 10 | 10I + 46I + 84A | 26 | 44.5 | 36.9 | 42.8 | 11 |
|  | n | 4 | 5 | 5 | 5 | 5 |
|  | Stdev | 11 | 20 | 24.7 | 9.7 | 5 |
| 11 | 46I + 71V | 3.7 | 1.4 | 1 | 0.6 | 2.2 |
|  | n | 5 | 5 | 5 | 5 | 4 |
|  | Stdev | 2.3 | 0.8 | 0.1 | 0.5 | 1.8 |
| 12 | 46I + 71V + 84V/I | 3.1 | 1.8 | 0.7 | 0.6 | 2.2 |
|  | n | 1 | 1 | 1 | 1 | 1 |
|  | Stdev |  |  |  |  |  |
| 13 | 46I + 71V + 84A | 56.5 | 102.2 | 59.9 | 47.7 | 23 |
|  | n | 6 | 6 | 6 | 6 | 5 |
|  | Stdev | 22.8 | 28 | 21.3 | 7.1 | 12.6 |
| 14 | 10F + 46I + 71V | 22.2 | 4.1 | 45.2 | 1.9 | 4.2 |
|  | n | 5 | 5 | 5 | 5 | 4 |
|  | Stdev | 1.9 | 2.1 | 16.1 | 1.1 | 2.2 |
| 15 | 10I + 46I + 71V + 84V | 50.5 | 45.6 | 57.1 | 15.9 | 17.8 |
|  | n | 14 | 14 | 14 | 14 | 12 |
|  | Stdev | 26.0 | 29.8 | 17.4 | 8.6 | 11.3 |
| 16 | 10I + 46I + 71V + 84A | 45.9 | 114.9 | 54.9 | 48.2 | 15.2 |
|  | n | 5 | 5 | 5 | 5 | 5 |
|  | Stdev | 28.3 | 42.9 | 21.8 | 13.1 | 2.5 |
| 17 | 10V + 46I + 71T + 84A | 57.9 | 91.9 | 51.2 | 48.2 | 39.8 |
|  | n | 5 | 5 | 5 | 5 | 5 |
|  | Stdev | 21.2 | 66.8 | 22.2 | 7.9 | 24.7 |
| 18 | 10I + 46I + 71V + 77I | 2.2 | 1.65 | 6.1 | 1.3 | 0.9 |
|  | n | 6 | 6 | 5 | 6 | 6 |
|  | Stdev | 2.6 | 0.7 | 1.8 | 0.8 | 0.4 |
| 19 | 10I + 46I + 71V + 77I + 84V | 2.2 | 3.1 | 2.8 | 2.5 | 1.4 |
|  | n | 3 | 3 | 3 | 3 | 3 |
|  | Stdev | 5.2 | 2.1 | 8.0 | 2.1 | 0.5 |
| 20 | 10I + 46I + 71V + 77I + 84A | 57.9 | 121.3 | 68.6 | 47.1 | 15 |
|  | n | 5 | 5 | 5 | 5 | 4 |
|  | Stdev | 22.2 | 71.4 | 22.1 | 6.1 | 6.6 |
| 21 | 10I + 33L/I + 46I + 71V + 77V/I + 84A | 31.4 | 38.6 | 63.1 | 44.7 | 10.9 |
|  | n | 5 | 5 | 6 | 6 | 5 |
|  | Stdev | 16 | 14.9 | 13.5 | 6 | 5.5 |

This table exemplifies that 84A mutation in a background of PR mutations confers an additional effect towards the protease inhibitors investigated. This indicates that even in a complex background of mutations the 84A mutation has an effect. The 84A mutation displays a different resistance profile compared with 84V, and teaches that not only the presence but also the exact identity of the mutation is important.

Example 9

Fold Increase in Resistance of Protease Inhibitors by the 84L Mutation (in a Background)

TABLE 10

Overview of the mean fold increase in resistance and the effect of the 84L mutation in the HIV-1 protease sequence. The fold increase in resistance is calculated from the increase in the mean IC50 of the drug relative to the mean IC50 of the same drug for a wild-type reference laboratory HIV-1 strain.

| # | Genotype | Indinavir | Ritonavir | Nelfinavir | Saquinavir | Amprenavir |
|---|---|---|---|---|---|---|
| 1 | 10I + 36I + 71V | 1.4 | 1.2 | 1.5 | 1.6 | 1.0 |
|  | n | 6 | 6 | 6 | 6 | 6 |
|  | Stdev | 0.5 | 0.5 | 0.6 | 0.8 | 0.6 |
| 2 | 10I + 36I + 71I + 84V | 1.0 | 1.5 | 0.8 | 0.8 | 1.1 |
|  | n | 1 | 1 | 1 | 1 | 1 |
|  | Stdev |  |  |  |  |  |

TABLE 10-continued

Overview of the mean fold increase in resistance and the effect of the 84L mutation in the HIV-1 protease sequence. The fold increase in resistance is calculated from the increase in the mean IC50 of the drug relative to the mean IC50 of the same drug for a wild-type reference laboratory HIV-1 strain.

| # | Genotype | Indinavir | Ritonavir | Nelfinavir | Saquinavir | Amprenavir |
|---|---|---|---|---|---|---|
| 3 | 10I + 36I + 71I + 84L | 3.7 | 0.8 | 39.4 | 10.2 | 0.3 |
|   | n | 4 | 5 | 5 | 5 | 5 |
|   | Stdev | 3.4 | 0.9 | 17.4 | 6.5 | 0.2 |

Genotyping of the sample displays that the 84L mutation is linked to protease resistance as compared to the result obtained from the 84V mutation in the same background.

Example 10

Fold Increase in Resistance of Protease Inhibitors by the 84C Mutation (and in a Background)

TABLE 11

Overview of the mean fold increase in resistance and the effect of the 84C mutation in the HIV protease sequence The fold increase in resistance is calculated from the increase in the mean IC50 of the drug relative to the mean IC50 of the same drug for a wild-type reference laboratory HIV-1 strain.

| # | Genotype | Indinavir | Ritonavir | Nelfinavir | Saquinavir | Amprenavir |
|---|---|---|---|---|---|---|
| 1 | WT | 0.9 | 0.6 | 0.7 | 0.9 | 1.0 |
|   | n | 6 | 6 | 6 | 6 | 6 |
|   | Stdev | 0.5 | 0.4 | 0.2 | 0.2 | 0.4 |
| 2 | 84V | 0.7 | 2.4 | 0.9 | 0.7 | 2.0 |
|   | n | 9 | 9 | 9 | 9 | 2 |
|   | Stdev | 0.9 | 2.0 | 0.8 | 0.6 | 0.9 |
| 3 | 84C | 2.7 | 2.9 | 51.2 | 26.4 | 5.9 |
|   | n | 5 | 5 | 5 | 4 | 5 |
|   | Stdev | 1.4 | 3.2 | 16.2 | 6.8 | 3.1 |
| 4 | 10I | 0.7 | 1.2 | 1.0 | 0.9 | 1.1 |
|   | n | 4 | 4 | 4 | 4 | 4 |
|   | Stdev | 0.2 | 0.7 | 0.6 | 0.3 | 0.4 |
| 5 | 10I + 84V | 1.8 | 6.5 | 2.0 | 2.7 | 1.2 |
|   | n | 3 | 3 | 3 | 3 | 3 |
|   | Stdev | 1.1 | 2.9 | 3.1 | 1.3 | 0.3 |
| 6 | 10I + 84C | 4.3 | 5.4 | 61.9 | 37.1 | 3.4 |
|   | n | 7 | 7 | 7 | 7 | 5 |
|   | Stdev | 3.2 | 3.8 | 18.0 | 16.5 | 1.5 |
| 7 | 77I | 0.4 | 0.4 | 0.9 | 0.3 | 0.6 |
|   | n | 3 | 3 | 3 | 3 | 3 |
|   | Stdev | 0.1 | 0.3 | 0.3 | 0.1 | 0.3 |
| 8 | 77I + 84V | 2.5 | 5.0 | 2.8 | 3.5 | 3.3 |
|   | n | 1 | 1 | 1 | 1 | 1 |
|   | Stdev |   |   |   |   |   |
| 9 | 77I + 84C | 3.1 | 2.8 | 61.9 | 18.1 | 2.2 |
|   | n | 5 | 4 | 5 | 5 | 5 |
|   | Stdev | 1.7 | 1.3 | 24.1 | 13.3 | 1.2 |
| 10 | 77I + 84C | 3.2 | 3.2 | 38.2 | 18.5 | 4.9 |
|   | n | 5 | 6 | 6 | 5 | 6 |
|   | Stdev | 2.9 | 1.4 | 22.3 | 12.1 | 2.5 |
| 11 | 10I + 24I + 36I + 46I + 71V + 84C | 7.5 | 47 | 51.7 | 46.4 | 12.8 |

The unique 84C mutation confers resistance towards protease inhibitors. The appearance of the 84C mutation is indicative of but not limited to Nelfinvir resistance.

Example 11

Fold Increase in Resistance of Protease Inhibitors by the 54M Mutation (in a Background)

TABLE 12

Influence of the 54M mutation in a background of different protease mutations and their corresponding effect on protease inhibitor resistance. The effect for the investigated compounds is expressed as a mean fold change in IC50 towards the mean IC50 determined for a wild type laboratory HIV strain.

| Virco ID | Genotype | Indinavir Fold change in $IC_{50}$ | Ritonavir Fold change in $IC_{50}$ | Nelfinavir Fold change in $IC_{50}$ | Saquinavir Fold change in $IC_{50}$ | Amprenavir Fold change in $IC_{50}$ |
|---|---|---|---|---|---|---|
| V021667 | 10I | 0.7 | 1.2 | 1.0 | 0.9 | 1.1 |
| V053832 | 10I + 33F | 0.4 | 2.9 | 1.6 | 0.5 | 0.6 |
| V052977 | 10I + 33F + 54M | 1.8 | 35.5 | 3.8 | 0.5 | 12.2 |
| V048878 | 10I + 33F + 54M + 71V + 77I + 90M | 5.2 | 17.2 | 7.3 | 4.0 | 13.7 |
| V048879 | 10I + 33F + 54M + 71V + 77I + 90M | 6.5 | 74.0 | 45.7 | 51.8 | 14.1 |
| V052978 | 10I + 33F + 54M + 71V + 90M | 5.4 | 17.9 | 29.1 | 9.9 | 19.3 |
| V055199 | 10I + 33F + 54M + 90M | 2.3 | 18.4 | 11.7 | 5.6 | 38.7 |
| V052953 | 10I + 33F + 77I | 0.8 | 1.1 | 0.9 | 1.2 | 1.5 |
| V048880 | 10I + 33F + 77I + 90M | 1.3 | 3.6 | 4.9 | 2.7 | 3.8 |
| V048877 | 10I + 33F + 77I + 90M | 2.9 | 20.5 | 9.4 | 1.5 | 7.9 |
| V052979 | 10I + 54M | 1.8 | 20.0 | 3.8 | 1.4 | 10.4 |
| V052982 | 10I + 54M + 71V + 77I + 90M | 2.4 | 13.4 | 10.1 | 4.2 | 3.1 |
| V052981 | 10I + 54M + 71V + 90M | 3.2 | 9.4 | 8.7 | 5.4 | 8.9 |
| V048869 | 10I + 54M + 77I + 90M | 7.1 | 20.0 | 28.5 | 5.1 | 9.3 |
| V052980 | 10I + 54M + 90M | 1.3 | 4.1 | 7.0 | 1.4 | 1.4 |
| V052942 | 10I + 71V | 0.6 | 0.6 | 0.9 | 0.8 | 0.5 |
| V052949 | 10I + 71V + 77I + 90M | 2.7 | 2.3 | 8.6 | 2.1 | 0.6 |
| V052948 | 10I + 71V + 90M | 8.6 | 10.5 | 9.0 | 4.8 | 2.0 |
| V030496 | 10I + 77I | 0.4 | 0.5 | 0.7 | 0.3 | 0.5 |
| V052947 | 10I + 77I + 90M | 2.9 | 6.9 | 8.2 | 3.9 | 1.2 |
| V052943 | 10I + 90M | 0.5 | 1.8 | 2.2 | 1.1 | 0.4 |
| V052944 | 10I + 90M | 0.5 | 1.5 | 1.4 | 0.7 | 0.7 |
| V052950 | 33F | 0.6 | 1.5 | 1.0 | 1.2 | 0.7 |
| V048872 | 33F + 54M + 77I + 90M | 3.2 | 8.7 | 7.4 | 5.2 | 30.3 |
| V048873 | 33F + 54M + 77I + 90M | 1.7 | 11.4 | 7.7 | 3.1 | 37.5 |
| V052955 | 33F + 71V + 90M | 5.3 | 77.9 | 36.6 | 20.4 | 2.7 |
| V052951 | 33F + 77I | 0.4 | 0.3 | 5.2 | 0.4 | 0.3 |
| V052954 | 33F + 77I + 90M | 1.7 | 2.2 | 5.9 | 1.7 | 2.1 |
| V052940 | 71V | 0.7 | 0.4 | 0.6 | 0.8 | 0.3 |
| V052946 | 71V + 90M | 0.9 | 2.0 | 3.0 | 1.4 | 0.5 |
| V19263 | 77I | 0.4 | 0.4 | 0.9 | 0.3 | 0.6 |
| V052945 | 77I + 90M | 0.6 | 1.9 | 3.0 | 1.4 | 0.3 |
| V20160 | WT | 0.9 | 0.6 | 0.7 | 0.9 | 1.0 |

Example 12

Fold Increase in Resistance of Protease Inhibitors by the 54L Mutation (in a Background)

TABLE 13

Influence of 54L mutation in a background of different protease mutations and their corresponding effect on protease inhibitor resistance. The effect for the investigated compounds is expressed as a mean fold change in $IC_{50}$ towards the mean $IC_{50}$ determined for a wild type laboratory HIV strain.

| Virco ID | Genotype | Indinavir Fold change in $IC_{50}$ | Ritonavir Fold change in $IC_{50}$ | Nelfinavir Fold change in $IC_{50}$ | Saquinavir Fold change in $IC_{50}$ | Amprenavir Fold change in $IC_{50}$ |
| --- | --- | --- | --- | --- | --- | --- |
| V021667 | 10I | 0.7 | 1.2 | 1.0 | 0.9 | 1.1 |
| V053832 | 10I + 33F | 0.4 | 2.9 | 1.6 | 0.5 | 0.6 |
| V048875 | 10I + 33F + 54L + 71V + 77I + 90M | 3.7 | 25.1 | 12.5 | 12.0 | 24.6 |
| V048874 | 10I + 33F + 54L + 71V + 77I + 90M | 2.1 | 21.3 | 14.5 | 4.6 | 32.1 |
| V052969 | 10I + 33F + 54L + 90M | 1.3 | 4.8 | 3.4 | 1.4 | 10.4 |
| V052953 | 10I + 33F + 77I | 0.8 | 1.1 | 0.9 | 1.2 | 1.5 |
| V048880 | 10I + 33F + 77I + 90M | 1.3 | 3.6 | 4.9 | 2.7 | 3.8 |
| V048877 | 10I + 33F + 77I + 90M | 2.9 | 20.5 | 9.4 | 1.5 | 7.9 |
| V052971 | 10I + 54L | 0.7 | 1.5 | 1.0 | 0.7 | 2.6 |
| V052976 | 10I + 54L + 71V + 77I + 90M | 1.7 | 6.5 | 8.9 | 1.8 | 2.0 |
| V048868 | 10I + 54L + 71V + 77I + 90M | 6.2 | 9.7 | 15.6 | 16.5 | 4.1 |
| V052975 | 10I + 54L + 71V + 90M | 10.2 | 30.5 | 41.3 | 24.2 | 6.2 |
| V052973 | 10I + 54L + 77I | 0.8 | 1.4 | 2.8 | 0.8 | 2.1 |
| V052974 | 10I + 54L + 90M | 1.7 | 3.6 | 2.6 | 1.1 | 1.2 |
| V052942 | 10I + 71V | 0.6 | 0.6 | 0.9 | 0.8 | 0.5 |
| V052949 | 10I + 71V + 77I + 90M | 2.7 | 2.3 | 8.6 | 2.1 | 0.6 |
| V052948 | 10I + 71V + 90M | 8.6 | 10.5 | 9.0 | 4.8 | 2.0 |
| V030496 | 10I + 77I | 0.4 | 0.5 | 0.7 | 0.3 | 0.5 |
| V052947 | 10I + 77I + 90M | 2.9 | 6.9 | 8.2 | 3.9 | 1.2 |
| V052943 | 10I + 90M | 0.5 | 1.8 | 2.2 | 1.1 | 0.4 |
| V052944 | 10I + 90M | 0.5 | 1.5 | 1.4 | 0.7 | 0.7 |
| V052968 | 10L/I + 33F/L + 54L + 77I | 1.3 | 4.7 | 3.5 | 1.5 | 2.9 |
| V052950 | 33F | 0.6 | 1.5 | 1.0 | 1.2 | 0.7 |
| V052955 | 33F + 71V + 90M | 5.3 | 77.9 | 36.6 | 20.4 | 2.7 |
| V052951 | 33F + 77I | 0.4 | 0.3 | 5.2 | 0.4 | 0.3 |
| V052954 | 33F + 77I + 90M | 1.7 | 2.2 | 5.9 | 1.7 | 2.1 |
| V052970 | 54L | 0.6 | 2.0 | 1.6 | 0.7 | 0.8 |
| V053854 | 54L + 71V | 1.7 | 2.3 | 5.9 | 0.9 | 5.0 |
| V052972 | 54L + 77I | 0.8 | 2.4 | 3.0 | 1.0 | 1.1 |
| V052940 | 71V | 0.7 | 0.4 | 0.6 | 0.8 | 0.3 |
| V052946 | 71V + 90M | 0.9 | 2.0 | 3.0 | 1.4 | 0.5 |
| V19263 | 77I | 0.4 | 0.4 | 0.9 | 0.3 | 0.6 |
| V052945 | 77I + 90M | 0.6 | 1.9 | 3.0 | 1.4 | 0.3 |
| V20160 | WT | 0.9 | 0.6 | 0.7 | 0.9 | 1.0 |

Example 13

Fold Increase in Resistance of Protease Inhibitors by the 54V Mutation (in a Background)

TABLE 14

Influence of 54V on protease resistance in a background of different mutations and their corresponding effect on drug resistance. The effect for the investigated compounds is expressed as a mean fold change in IC50 towards the mean IC50 determined for a wild type laboratory HIV strain.

| Virco ID | Genotype | Indinavir Fold change in $IC_{50}$ | Ritonavir Fold change in $IC_{50}$ | Nelfinavir Fold change in $IC_{50}$ | Saquinavir Fold change in $IC_{50}$ | Amprenavir Fold change in $IC_{50}$ |
| --- | --- | --- | --- | --- | --- | --- |
| V021667 | 10I | 0.7 | 1.2 | 1.0 | 0.9 | 1.1 |
| V053832 | 10I + 33F | 0.4 | 2.9 | 1.6 | 0.5 | 0.6 |
| 214846 | 10I + 33F + 54V + 71V + 77I + 90M | 13.8 | 57.6 | 43.5 | 27.8 | 4.2 |

TABLE 14-continued

Influence of 54V on protease resistance in a background of different mutations and their corresponding effect on drug resistance. The effect for the investigated compounds is expressed as a mean fold change in IC50 towards the mean IC50 determined for a wild type laboratory HIV strain.

| Virco ID | Genotype | Indinavir Fold change in IC$_{50}$ | Ritonavir Fold change in IC$_{50}$ | Nelfinavir Fold change in IC$_{50}$ | Saquinavir Fold change in IC$_{50}$ | Amprenavir Fold change in IC$_{50}$ |
|---|---|---|---|---|---|---|
| V052960 | 10I + 33F + 54V + 71V + 90M | 9.9 | 70.9 | 40.7 | 21.8 | 6.4 |
| V052959 | 10I + 33F + 54V + 77I + 90M | 12.8 | 28.5 | 7.5 | 1.0 | 7.0 |
| V052958 | 10I + 33F + 54V + 77I + 90M | 16.3 | 16.6 | 4.8 | 1.0 | 7.8 |
| V052957 | 10I + 33F + 54V + 90M | 1.4 | 13.9 | 6.9 | 1.6 | 5.2 |
| V052953 | 10I + 33F + 77I | 0.8 | 1.1 | 0.9 | 1.2 | 1.5 |
| V048880 | 10I + 33F + 77I + 90M | 1.3 | 3.6 | 4.9 | 2.7 | 3.8 |
| V048877 | 10I + 33F + 77I + 90M | 2.9 | 20.5 | 9.4 | 1.5 | 7.9 |
| V052962 | 10I + 54V | 0.8 | 1.0 | 0.6 | 0.9 | 0.5 |
| V052967 | 10I + 54V + 71V + 77I + 90M | 0.4 | 0.7 | 0.8 | 0.6 | 0.4 |
| V052966 | 10I + 54V + 71V + 90M | 7.7 | 44.5 | 55.4 | 28.6 | 1.5 |
| V052965 | 10I + 54V + 77I + 90M | 8.2 | 12.5 | 15.1 | 6.3 | 0.7 |
| V052942 | 10I + 71V | 0.6 | 0.6 | 0.9 | 0.8 | 0.5 |
| V052949 | 10I + 71V + 77I + 90M | 2.7 | 2.3 | 8.6 | 2.1 | 0.6 |
| V052948 | 10I + 71V + 90M | 8.6 | 10.5 | 9.0 | 4.8 | 2.0 |
| V030496 | 10I + 77I | 0.4 | 0.5 | 0.7 | 0.3 | 0.5 |
| V052947 | 10I + 77I + 90M | 2.9 | 6.9 | 8.2 | 3.9 | 1.2 |
| V052943 | 10I + 90M | 0.5 | 1.8 | 2.2 | 1.1 | 0.4 |
| V052944 | 10I + 90M | 0.5 | 1.5 | 1.4 | 0.7 | 0.7 |
| V052950 | 33F | 0.6 | 1.5 | 1.0 | 1.2 | 0.7 |
| V053831 | 33F + 54V | 5.4 | 129.7 | 5.9 | 1.0 | 7.5 |
| V053358 | 33F + 54V + 77I + 90M | 1.2 | 4.9 | 2.1 | 1.3 | 1.0 |
| V048876 | 33F + 54V + 77I + 90M | 0.6 | 5.6 | 1.6 | 1.5 | 1.1 |
| V052955 | 33F + 71V + 90M | 5.3 | 77.9 | 36.6 | 20.4 | 2.7 |
| V052951 | 33F + 77I | 0.4 | 0.3 | 5.2 | 0.4 | 0.3 |
| V052954 | 33F + 77I + 90M | 1.7 | 2.2 | 5.9 | 1.7 | 2.1 |
| V052961 | 54V | 0.7 | 1.2 | 1.0 | 1.0 | 0.5 |
| V052964 | 54V + 71V + 90M | 0.7 | 7.1 | 3.3 | 1.4 | 0.3 |
| V052963 | 54V + 77I + 90M | 1.2 | 2.0 | 3.2 | 1.3 | 0.5 |
| V052940 | 71V | 0.7 | 0.4 | 0.6 | 0.8 | 0.3 |
| V052946 | 71V + 90M | 0.9 | 2.0 | 3.0 | 1.4 | 0.5 |
| V19263 | 77I | 0.4 | 0.4 | 0.9 | 0.3 | 0.6 |
| V052945 | 77I + 90M | 0.6 | 1.9 | 3.0 | 1.4 | 0.3 |
| V20160 | WT | 0.9 | 0.6 | 0.7 | 0.9 | 1.0 |

All references, patents, and patent applications cited herein are incorporated by reference in their entirety.

It will be apparent to those skilled in the art that various modifications and variations can be made in the compositions and methods of the present invention without departing from the spirit or scope of the invention. Thus, it is intended that the present description cover the modifications and variations of this invention provided that they come within the scope of the appended claims and their equivalents.

---

The invention claimed is:

1. A method of evaluating the effectiveness of a protease inhibitor as an antiviral therapy of an HIV-infected patient, comprising:
    (a) collecting a sample from an HIV-infected patient;
    (b) amplifying viral genomic sequences using primers targeting the HIV protease gene and determining whether the sample comprises a nucleic acid encoding a HIV protease having the mutation I84C combined with at least one additional mutation selected from L10I, K20R, K20T, L24I, L33F, L33I, M36I, M46L, A71T, A71V, V77I, V82I, or L90M, wherein the codon position number is compared to the sequence of reference wild-type HIV IIIB/LAI; and
    (c) using the presence of said at least one mutations of step b) to evaluate the effectiveness of said antiviral therapy.

2. A method of evaluating the effectiveness of a protease inhibitor as an antiviral therapy of an HIV-infected patient, comprising:
    (a) collecting a sample from an HIV-infected patient;
    (b) amplifying viral genomic sequences using primers targeting the HIV protease gene and determining whether the sample comprises a nucleic acid encoding a HIV protease having the mutation I84C combined with at least one additional mutation in at least one of codons L10 and L90, wherein the codon position number is compared to the sequence of reference wild-type HIV IIIB/LAI; and
    (c) using the presence of said at least one mutations of step b) to evaluate the effectiveness of said antiviral therapy.

* * * * *

SEQUENCE LISTING

<160> NUMBER OF SEQ ID NOS: 1

<210> SEQ ID NO 1
<211> LENGTH: 9719
<212> TYPE: DNA
<213> ORGANISM: Human immunodeficiency virus type 1

<400> SEQUENCE: 1

```
tggaagggct aattcactcc caacgaagac aagatatcct tgatctgtgg atctaccaca      60
cacaaggcta cttccctgat tagcagaact acacaccagg gccagggatc agatatccac     120
tgacctttgg atggtgctac aagctagtac cagttgagcc agagaagtta gaagaagcca     180 acaaggaga gaacaccagc ttgttacacc ctgtgagcct gcatggaatg gatgacccgg     240
```

```
agagagaagt gttagagtgg aggtttgaca gccgcctagc atttcatcac atggcccgag    300
agctgcatcc ggagtacttc aagaactgct gacatcgagc ttgctacaag gactttccg    360 ctggggactt tccagggagg cgtggcctgg gcgggactgg ggagtggcga gccctcagat    420
cctgcatata agcagctgct ttttgcctgt actgggtctc tctggttaga ccagatctga    480
gcctgggagc tctctggcta actagggaac ccactgctta agcctcaata aagcttgcct    540
tgagtgcttc aagtagtgtg tgcccgtctg ttgtgtgact ctggtaacta gagatccctc    600
agaccctttt agtcagtgtg gaaaatctct agcagtggcg cccgaacagg gacctgaaag    660
cgaaagggaa accagaggag ctctctcgac gcaggactcg gcttgctgaa gcgcgcacgg    720
caagaggcga gggcggcga ctggtgagta cgccaaaaat tttgactagc ggaggctaga    780
aggagagaga tgggtgcgag agcgtcagta ttaagcgggg gagaattaga tcgatgggaa    840
aaaattcggt taaggccagg gggaaagaaa aaatataaat taaaacatat agtatgggca    900
agcagggagc tagaacgatt cgcagttaat cctggcctgt tagaaacatc agaaggctgt    960
agacaaatac tgggacagct acaaccatcc cttcagacag gatcagaaga acttagatca    1020
ttatataata cagtagcaac cctctattgt gtgcatcaaa ggatagagat aaaagacacc    1080
aaggaagctt tagacaagat agaggaagag caaaacaaaa gtaagaaaaa agcacagcaa    1140
gcagcagctg acacaggaca cagcaatcag gtcagccaaa attaccctat agtgcagaac    1200
atccaggggc aaatggtaca tcaggccata tcacctagaa cttttaaatgc atgggtaaaa    1260 gtagtagaag agaaggcttt cagcccagaa gtgatacccca tgttttcagc attatcagaa    1320
ggagccaccc cacaagattt aaacaccatg ctaaacacag tggggggaca tcaagcagcc    1380
atgcaaatgt taaagagac catcaatgag gaagctgcag aatgggatag agtgcatcca    1440
gtgcatgcag ggcctattgc accaggccag atgagagaac caaggggaag tgacatagca    1500
ggaactacta gtacccttca ggaacaaata ggatggatga caaataatcc acctatccca    1560
gtaggagaaa tttataaaag atggataatc ctgggattaa ataaaatagt aagaatgtat    1620
agccctacca gcattctgga cataagacaa ggaccaaagg aaccctttag agactatgta    1680
gaccggttct ataaaactct aagagccgag caagcttcac aggaggtaaa aaattggatg    1740
acagaaacct tgttggtcca aaatgcgaac ccagattgta agactatttt aaaagcattg    1800
ggaccagcgg ctacactaga agaaatgatg acagcatgtc agggagtagg aggacccggc    1860
cataaggcaa gagttttggc tgaagcaatg agccaagtaa caaattcagc taccataatg    1920
atgcagagag gcaattttag gaaccaaaga aagattgtta agtgtttcaa ttgtggcaaa    1980
gaagggcaca cagccagaaa ttgcagggcc cctaggaaaa agggctgttg gaaatgtgga    2040
aaggaaggac accaaatgaa agattgtact gagagacagg ctaattttt agggaagatc    2100 tggccttcct acaagggaag gccagggaat tttcttcaga gcagaccaga gccaacagcc    2160
ccaccagaag agagcttcag gtctggggta gagacaacaa ctcccccctca gaagcaggag    2220 ccgatagaca aggaactgta tcctttaact tccctcaggt cactctttgg caacgacccc    2280
tcgtcacaat aaagataggg gggcaactaa aggaagctct attagataca ggagcagatg    2340
atacagtatt agaagaaatg agtttgccag gaagatggaa accaaaaatg ataggggaa    2400 ttggaggttt tatcaaagta agacagtatg atcagatact catagaaatc tgtggacata    2460
aagctatagg tacagtatta gtaggaccta cacctgtcaa cataattgga agaaatctgt    2520
tgactcagat tggttgcact ttaaattttc ccattagccc tattgagact gtaccagtaa    2580
aattaaagcc aggaatggat ggcccaaaag ttaaacaatg gccattgaca gaagaaaaaa    2640
```

```
taaaagcatt agtagaaatt tgtacagaga tggaaaagga agggaaaatt tcaaaaattg    2700
ggcctgaaaa tccatacaat actccagtat ttgccataaa gaaaaaagac agtactaaat    2760
ggagaaaatt agtagatttc agagaactta ataagagaac tcaagacttc tgggaagttc    2820
aattaggaat accacatccc gcagggttaa aaagaaaaa atcagtaaca gtactggatg     2880
tgggtgatgc atattttca gttcccttag atgaagactt caggaagtat actgcattta     2940
ccatacctag tataaacaat gagacaccag ggattagata tcagtacaat gtgcttccac    3000
agggatggaa aggatcacca gcaatattcc aaagtagcat gacaaaaatc ttagagcctt    3060
ttagaaaaca aaatccagac atagttatct atcaatacat ggatgatttg tatgtaggat    3120
ctgacttaga aatagggcag catagaacaa aaatagagga gctgagacaa catctgttga    3180
ggtggggact taccacacca gacaaaaaac atcagaaaga acctccattc ctttggatgg    3240
gttatgaact ccatcctgat aaatggacag tacagcctat agtgctgcca gaaaaagaca    3300
gctggactgt caatgacata cagaagttag tggggaaatt gaattgggca agtcagattt    3360
acccagggat taaagtaagg caattatgta aactccttag aggaaccaaa gcactaacag    3420
aagtaatacc actaacagaa gaagcagagc tagaactggc agaaaacaga gagattctaa    3480
aagaaccagt acatggagtg tattatgacc catcaaaaga cttaatagca gaaatacaga    3540 agcagggca aggccaatgg acatatcaaa tttatcaaga gccatttaaa aatctgaaaa    3600
caggaaaata tgcaagaatg aggggtgccc acactaatga tgtaaaacaa ttaacagagg    3660
cagtgcaaaa aataaccaca gaaagcatag taatatgggg aaagactcct aaatttaaac    3720
tgcccataca aaaggaaaca tgggaaacat ggtggacaga gtattggcaa gccacctgga    3780
ttcctgagtg ggagtttgtt aatacccctc ccttagtgaa attatggtac cagttagaga    3840
aagaacccat agtaggagca gaaaccttct atgtagatgg ggcagctaac agggagacta    3900
aattaggaaa agcaggatat gttactaata gaggaagaca aaaagttgtc accctaactg    3960
acacaacaaa tcagaagact gagttacaag caatttatct agctttgcag gattcgggat    4020
tagaagtaaa catagtaaca gactcacaat atgcattagg aatcattcaa gcacaaccag    4080
atcaaagtga atcagagtta gtcaatcaaa taatagagca gttaataaaa aaggaaaagg    4140
tctatctggc atgggtacca gcacacaaag gaattggagg aaatgaacaa gtagataaat    4200
tagtcagtgc tggaatcagg aaagtactat ttttagatgg aatagataag gcccaagatg    4260
aacatgagaa atatcacagt aattggagag caatggctag tgattttaac ctgccacctg    4320
tagtagcaaa agaaatagta gccagctgtg ataaatgtca gctaaaagga gaagccatgc    4380
atggacaagt agactgtagt ccaggaatat ggcaactaga ttgtacacat ttagaaggaa    4440
aagttatcct ggtagcagtt catgtagcca gtggatatat agaagcagaa gttattccag    4500
cagaaacagg gcaggaaaca gcatattttc ttttaaaatt agcaggaaga tggccagtaa    4560
aaacaataca tactgacaat ggcagcaatt tcaccggtgc tacggttagg gccgcctgtt    4620
ggtgggcggg aatcaagcag gaatttggaa ttccctacaa tccccaaagt caaggagtag    4680
tagaatctat gaataaagaa ttaaagaaaa ttataggaca ggtaagagat caggctgaac    4740
atcttaagac agcagtacaa atggcagtat tcatccacaa ttttaaaaga aaagggggga    4800 ttgggggta cagtgcaggg gaaagaatag tagacataat agcaacagac atacaaacta    4860
aagaattaca aaaacaaatt acaaaaattc aaaattttcg ggtttattac agggacagca    4920
gaaatccact ttggaaagga ccagcaaagc tcctctggaa aggtgaaggg gcagtagtaa    4980
tacaagataa tagtgacata aaagtagtgc caagaagaaa agcaaagatc attagggatt    5040
```

```
atggaaaaca gatggcaggt gatgattgtg tggcaagtag acaggatgag gattagaaca    5100
tggaaaagtt tagtaaaaca ccatatgtat gtttcaggga aagctagggg atggttttat    5160
agacatcact atgaaagccc tcatccaaga ataagttcag aagtacacat cccactaggg    5220
gatgctagat tggtaataac aacatattgg ggtctgcata caggagaaag agactggcat    5280
ttgggtcagg gagtctccat agaatggagg aaaaagagat atagcacaca agtagaccct    5340
gaactagcag accaactaat tcatctgtat tactttgact gtttttcaga ctctgctata    5400
agaaaggcct tattaggaca catagttagc cctaggtgtg aatatcaagc aggacataac    5460
aaggtaggat ctctacaata cttggcacta gcagcattaa taacaccaaa aaagataaag    5520
ccacctttgc ctagtgttac gaaactgaca gaggatagat ggaacaagcc ccagaagacc    5580
aagggccaca gagggagcca cacaatgaat ggacactaga gcttttagag gagcttaaga    5640
atgaagctgt tagacatttt cctaggattt ggctccatgg cttagggcaa catatctatg    5700
aaacttatgg ggatacttgg gcaggagtgg aagccataat aagaattctg caacaactgc    5760
tgtttatcca ttttcagaat tgggtgtcga catagcagaa taggcgttac tcgacagagg    5820
agagcaagaa atggagccag tagatcctag actagagccc tggaagcatc caggaagtca    5880
gcctaaaact gcttgtacca attgctattg taaaaagtgt tgctttcatt gccaagtttg    5940
tttcataaca aaagccttag gcatctccta tggcaggaag aagcggagac agcgacgaag    6000
agctcatcag aacagtcaga ctcatcaagc ttctctatca aagcagtaag tagtacatgt    6060
aacgcaacct ataccaatag tagcaatagt agcattagta gtagcaataa taatagcaat    6120
agttgtgtgg tccatagtaa tcatagaata taggaaaata ttaagacaaa gaaaaataga    6180
caggttaatt gatagactaa tagaaagagc agaagacagt ggcaatgaga gtgaaggaga    6240
aatatcagca cttgtggaga tgggggtgga gatgggcac catgctcctt gggatgttga    6300
tgatctgtag tgctacagaa aaattgtggg tcacagtcta ttatgggta cctgtgtgga    6360
aggaagcaac caccactcta ttttgtgcat cagatgctaa agcatatgat acagaggtac    6420
ataatgtttg ggccacacat gcctgtgtac ccacagaccc caacccacaa gaagtagtat    6480
tggtaaatgt gacagaaaat tttaacatgt ggaaaaatga catggtagaa cagatgcatg    6540
aggatataat cagtttatgg gatcaaagcc taaagccatg tgtaaaatta accccactct    6600
gtgttagttt aaagtgcact gatttgaaga atgatactaa taccaatagt agtagcggga    6660
gaatgataat ggagaaagga gagataaaaa actgctcttt caatatcagc acaagcataa    6720
gaggtaaggt gcagaaagaa tatgcatttt tttataaact tgatataata ccaatagata    6780
atgatactac cagctataag ttgacaagtt gtaacacctc agtcattaca caggcctgtc    6840
caaaggtatc ctttgagcca attcccatac attattgtgc cccggctggt tttgcgattc    6900
taaaatgtaa taataagacg ttcaatggaa caggaccatg tacaaatgtc agcacagtac    6960
aatgtacaca tggaattagg ccagtagtat caactcaact gctgttaaat ggcagtctag    7020
cagaagaaga ggtagtaatt agatctgtca atttcacgga caatgctaaa accataatag    7080
tacagctgaa cacatctgta gaaattaatt gtacaagacc caacaacaat acaagaaaaa    7140
gaatccgtat ccagagagga ccagggagag catttgttac aataggaaaa ataggaaata    7200
tgagacaagc acattgtaac attagtagag caaaatggaa taacacttta aaacagatag    7260
ctagcaaatt aagagaacaa tttggaaata taaaacaat aatctttaag caatcctcag    7320
gaggggaccc agaaattgta acgcacagtt ttaattgtgg aggggaattt ttctactgta    7380
attcaacaca actgtttaat agtacttggt ttaatagtac ttggagtact gaagggtcaa    7440
```

```
ataacactga aggaagtgac acaatcaccc tcccatgcag aataaaacaa attataaaca   7500
tgtggcagaa agtaggaaaa gcaatgtatg cccctcccat cagtggacaa attagatgtt   7560
catcaaatat tacagggctg ctattaacaa gagatggtgg taatagcaac aatgagtccg   7620
agatcttcag acctggagga ggagatatga gggacaattg gagaagtgaa ttatataaat   7680
ataaagtagt aaaaattgaa ccattaggag tagcacccac caaggcaaag agaagagtgg   7740
tgcagagaga aaaagagca gtgggaatag gagctttgtt ccttgggttc ttgggagcag   7800
caggaagcac tatgggcgca gcctcaatga cgctgacggt acaggccaga caattattgt   7860
ctggtatagt gcagcagcag aacaatttgc tgagggctat tgaggcgcaa cagcatctgt   7920
tgcaactcac agtctgggc atcaagcagc tccaggcaag aatcctggct gtggaaagat   7980
acctaaagga tcaacagctc ctggggattt ggggttgctc tggaaaactc atttgcacca   8040
ctgctgtgcc ttggaatgct agttggagta ataaatctct ggaacagatt tggaatcaca   8100
cgacctggat ggagtgggac agagaaatta acaattacac aagcttaata cactccttaa   8160
ttgaagaatc gcaaaccag caagaaaaga tgaacaaga attattggaa ttagataaat   8220
gggcaagttt gtgaattgg tttaacataa caaattggct gtggtatata aaattattca   8280
taatgatagt aggaggcttg gtaggtttaa gaatagtttt tgctgtactt tctatagtga   8340
atagagttag gcaggatat tcaccattat cgtttcagac ccacctccca accccgaggg   8400
gacccgacag gcccgaagga atagaagaag aaggtggaga gagagacaga gacagatcca   8460
ttcgattagt gaacggatcc ttggcactta tctgggacga tctgcggagc ctgtgcctct   8520
tcagctacca ccgcttgaga gacttactct tgattgtaac gaggattgtg gaacttctgg   8580
gacgcagggg gtgggaagcc ctcaaatatt ggtggaatct cctacagtat tggagtcagg   8640
aactaaagaa tagtgctgtt agcttgctca atgccacagc catagcagta gctgaggga   8700 cagatagggt tatagaagta gtacaaggag cttgtagagc tattcgccac atacctagaa   8760
gaataagaca gggcttggaa aggattttgc tataagatgg gtggcaagtg gtcaaaaagt   8820
agtgtgattg gatggcctac tgtaagggaa agaatgagac gagctgagcc agcagcagat   8880
agggtgggag cagcatctcg agacctggaa aaacatggag caatcacaag tagcaataca   8940
gcagctacca atgctgcttg tgcctggcta aagcacaag aggaggagga ggtgggtttt   9000
ccagtcacac ctcaggtacc tttaagacca atgacttaca aggcagctgt agatcttagc   9060 cacttttaa aagaaaaggg gggactggaa gggctaattc actcccaaag aagacaagat   9120
atccttgatc tgtggatcta ccacacacaa ggctacttcc ctgattagca gaactacaca   9180
ccagggccag gggtcagata tccactgacc tttggatggt gctacaagct agtaccagtt   9240
gagccagata agatagaaga ggccaataaa ggagagaaca ccagcttgtt acaccctgtg   9300
agcctgcatg gatggatga cccggagaga gaagtgttag agtggaggtt tgacagccgc   9360
ctagcatttc atcacgtggc ccgagagctg catccggagt acttcaagaa ctgctgacat   9420
cgagcttgct acaagggact ttccgctggg gactttccag ggaggcgtgg cctgggcggg   9480
actggggagt ggcgagccct cagatcctgc atataagcag ctgctttttg cctgtactgg   9540
gtctctctgg ttagaccaga tctgagcctg ggagctctct ggctaactag ggaacccact   9600
gcttaagcct caataaagct tgccttgagt gcttcaagta gtgtgtgccc gtctgttgtg   9660
tgactctggt aactagagat ccctcagacc cttttagtca gtgtggaaaa tctctagca    9719
```